US009670174B2

(12) United States Patent
Stensrud

(10) Patent No.: US 9,670,174 B2
(45) Date of Patent: Jun. 6, 2017

(54) MONO- AND DIALKYL ETHERS OF FURAN-2,5-DIMETHANOL AND (TETRA-HYDROFURAN-2,5-DIYL)DIMETHANOL AND AMPHIPHILIC DERIVATIVES THEREOF

(71) Applicant: Archer Daniels Midland Company, Decatur, IL (US)

(72) Inventor: Kenneth Stensrud, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/038,066

(22) PCT Filed: Dec. 12, 2014

(86) PCT No.: PCT/US2014/070021
§ 371 (c)(1),
(2) Date: May 20, 2016

(87) PCT Pub. No.: WO2015/094970
PCT Pub. Date: Jun. 25, 2015

(65) Prior Publication Data

US 2016/0297785 A1 Oct. 13, 2016

Related U.S. Application Data

(60) Provisional application No. 61/918,239, filed on Dec. 19, 2013.

(51) Int. Cl.

| | |
|---|---|
| *C07D 307/12* | (2006.01) |
| *C07D 307/42* | (2006.01) |
| *C07D 307/14* | (2006.01) |
| *C07D 307/52* | (2006.01) |

(52) U.S. Cl.
CPC ......... *C07D 307/12* (2013.01); *C07D 307/14* (2013.01); *C07D 307/42* (2013.01); *C07D 307/52* (2013.01)

(58) Field of Classification Search
None
See application file for complete search history.

(56) References Cited

U.S. PATENT DOCUMENTS 4,619,917 A * 10/1986 Lee .................... C07F 9/65586 514/77
5,208,352 A * 5/1993 Chen .................... C07D 307/12 549/502

* cited by examiner

*Primary Examiner* — Timothy R Rozof
(74) *Attorney, Agent, or Firm* — Vincent T. Kung

(57) ABSTRACT

Linear mono- and dialkyl ethers of furan-2,5-dimethanol (FDM) and/or 2,5-bis(hydroxymethyl)tetrahydrofuran (bHMTHF), methods for their preparation, and derivative chemical compounds thereof are described. In general, the synthesis process entails a reaction of FDM or bHMTHFs in a polar aprotic organic solvent having a permittivity ( )>8, at a temperature ranging from about −25 C to about 100 C, with either a) an unhindered Brnsted base with a pKa?15 or b) a hindered Brnsted base having minimum pKa of about 16, and a nucleophile.

27 Claims, No Drawings

MONO- AND DIALKYL ETHERS OF FURAN-2,5-DIMETHANOL AND (TETRA-HYDROFURAN-2,5-DIYL)DIMETHANOL AND AMPHIPHILIC DERIVATIVES THEREOF

BENEFIT OF PRIORITY

The present application is a national stage entry of International Application No. PCT/US2014/070021, filed Dec. 12, 2014, which claims benefit of priority of U.S. Provisional Application No. 61/918,239, filed Dec. 19, 2013, the contents of which are incorporated herein by reference.

FIELD OF INVENTION

The present disclosure relates to certain cyclic bi-functional materials that are useful as monomers in polymer synthesis, as well as intermediate chemical compounds. In particular, the present invention pertains to ethers of furan-2,5-dimethanol (FDM) and/or (tetrahydrofuran-2,5-diyl)dimethanol (bHMTHF), methods for their preparation, and derivative chemical compounds thereof.

BACKGROUND

Research into renewable, bio-based surrogates for petroleum-based platform chemicals is on the rise in view of growing concerns about the impact of climate change and the gradual depletion of fossil fuels. Sugars are ubiquitous in agricultural materials, and hence are rational precursors for empirical innovations in the "green" materials area. Organic compounds that are readily derived from sugars include furans, robust cyclic ethers that possess structural features which can be useful for making certain polymers, pharmaceuticals, or solvents, among other industrial constituents.

A related compound that has received considerable attention of late is 5-(hydroxymethyl)furfural (HMF), (Figure 1), a salient dehydration product of the abundant, inexpensive monosaccharide, fructose.

FIG. 1. Chemical structure of HMF

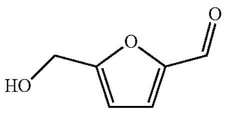

HMF is a versatile chemical antecedent to various furanic ring-based derivatives that are known intermediates for a multitude of chemical syntheses, and as plausible surrogates for aromatic hydrocarbons that derive from petroleum resources. Due to HMF's diverse functionalities, some have proposed that HMF be used to produce a wide range of commodities such as polymers, solvents, surfactants, pharmaceuticals, and plant protection agents. As alternates, derivatives of HMF are comparable to benzene-based aromatic compounds or to other compounds containing a furan or tetrahydrofuran (THF). HMF and 2,5-disubstituted furans and THF analogs, therefore, have great potential in the field of intermediate chemicals from renewable agricultural resources.

HMF itself, however, is rather unsuitable as a chemical intermediate substrate, given its propensity to decompose under thermo-oxidative conditions. Thus, one should look to derivatives of HMF for practical commercial utility. One derivative is furan-2,5-dimethanol (abbreviated as FDM) (Scheme 1), which is produced from partial hydrogenation (aldehyde reduction) of HMF.

Scheme 1.-FDM B from partial hydrogenation of HMF A

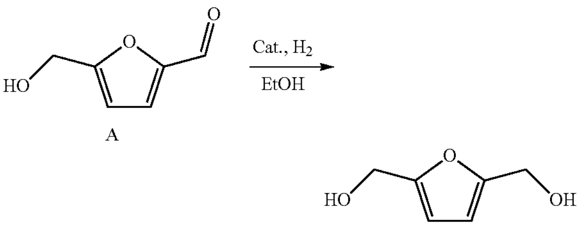

A

B

Another derivative is 2,5-bis(hydroxymethyl)tetrahydrofuran (abbreviated as bHMTHF), a saturated analog produced in a 9:1 cis (B):trans (C) diastereomeric ratio when both the ring and aldehyde moieties of HMF are reduce completely (Scheme 2).

Scheme 2. - bHMTHFs from the exhaustive reduction of HMF

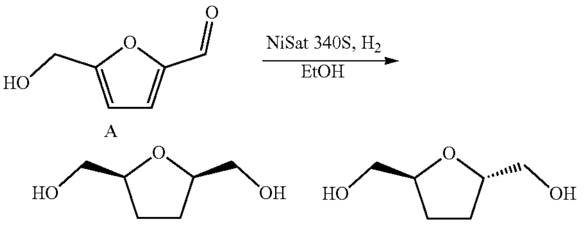

A

B, 90%

C, 10%

These materials can be of value as a molecular antecedent, for example, to polyesters, polyurethane foams, FDCA, plasticizers, additives, lubricants, and amphiphiles.

To become market competitive with petroleum products, however, the preparation of HMF derivatives from standard agricultural raw materials, such as sugars, need to become economically feasible in terms of cost. Heretofore, research for chemical derivatives using FDM and/or bHMTHFs has received limited attention due in part to the great cost and relative paucity (e.g., ~$200 per gram commercially) of the compounds. Recently, a need has arisen for a way to unlock the potential of FDM and bHMTHFs and their derivative compounds, as these chemical entities have gained attention as valuable glycolic antecedents for the preparation of polymers, solvents, additives, lubricants, and plasticizers, etc. Furthermore, the inherent, immutable chirality of bHMTHFs makes these compounds useful as potential species for pharmaceutical applications or candidates in the emerging chiral auxiliary field of asymmetric organic synthesis. Given the potential uses, a cost efficient and simple process that can synthesis derivatives from FDM and/or bHMTHFs would be appreciated by manufacturers of both industrial and specialty chemicals alike as a way to better utilize biomass-derived carbon resources.

SUMMARY OF THE INVENTION

The present disclosure describes, in part, linear mono- and di-alkyl ethers of furan-2,5-dimethanol (FDM) and/or 2,5- bis(hydroxymethyl)tetrahydrofuran (bHMTHF), and a process for their synthesis. Generally, the process includes contacting either FDM or bHMTHF in a polar aprotic organic solvent having a permittivity (∈)>8, at a temperature ranging from about −25° C. to about 100° C., with either a) an unhindered Brønsted base having a difference in pKa (ΔpKa)≥15 relative to the pKa of a hydroxyl group of either FDM or bHMTHF or b) a hindered Brønsted base and a nucleophile.

In a particular embodiment, the present disclosure provides a method of preparing a mono-ether involving: contacting FDM with a Brønsted base and one or less molar equivalents of an alkyl-X species according to the following:

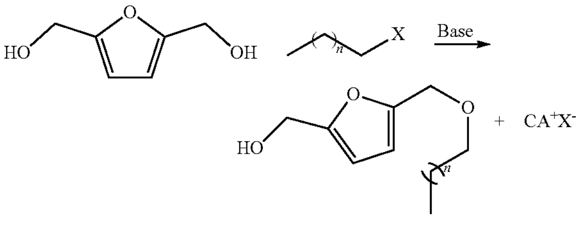

wherein: "X" is the leaving group (nucleofuge), "n" is an integer from 5 to 25, and "CA" is a conjugate acid. The resultant mono-ether of FDM can be, for example, at least one of the following compounds:

a. (5-((octadecyloxy)methyl)furan-2-yl)methanol

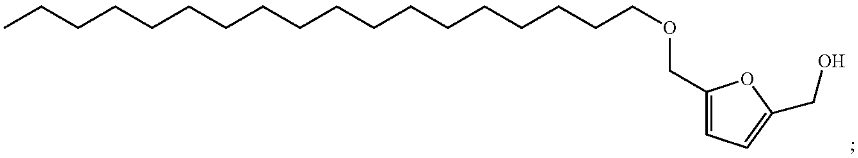 [SMILES: CCCCCCCCCCCCCCCCCCOCc1ccc(CO)o1]

;

b. (5-((dodecyloxy)methyl)furan-2-yl)methanol

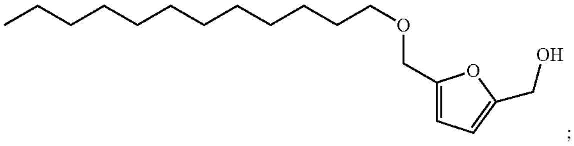 [SMILES: CCCCCCCCCCCCOCc1ccc(CO)o1]

;

c. (5-((hexyloxy)methyl)furan-2-yl)methanol

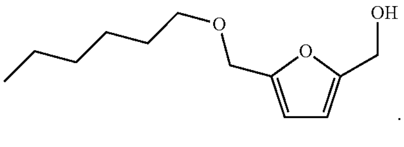

.

In an embodiment for preparing di-ethers, the method involves: contacting FDM with a Brønsted base and a minimum of 2 molar equivalents of an alkyl-X species according to the following:

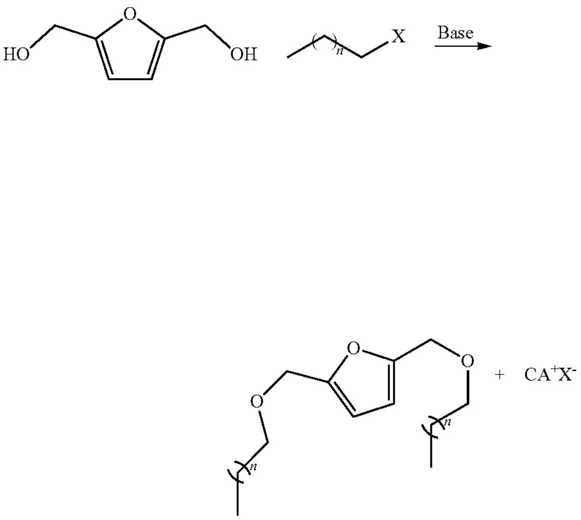

wherein: "X" is the nucleofuge, "n" is an integer from 5 to 25, and "CA" is a conjugate acid. The resultant di-ether of FDM can be, for instance, at least one of the following compounds:

a. 2,5-bis((hexyloxy)methyl)furan

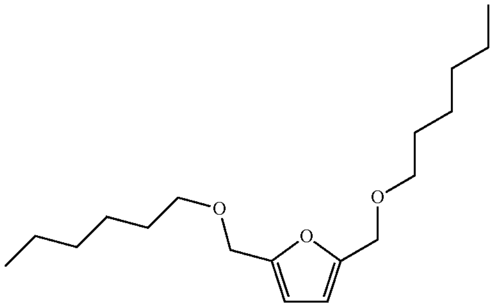

;

b. 2,5-bis((dodecyloxy)methyl)furan

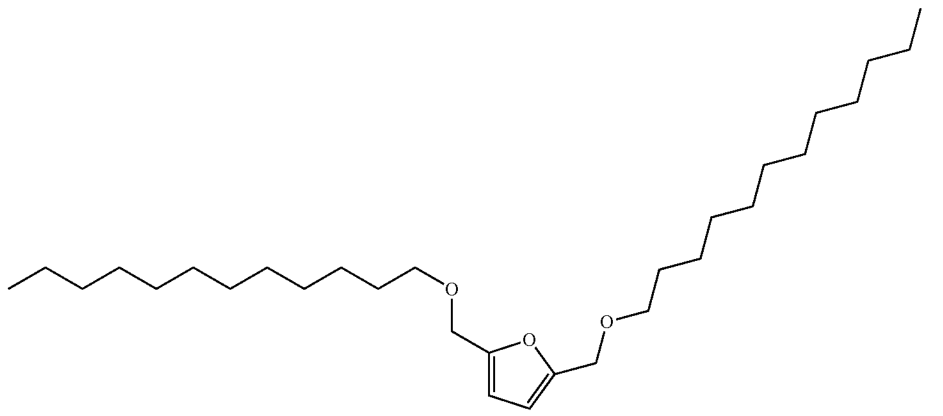

;

c. 2,5-bis((octadecyloxy)methyl)furan

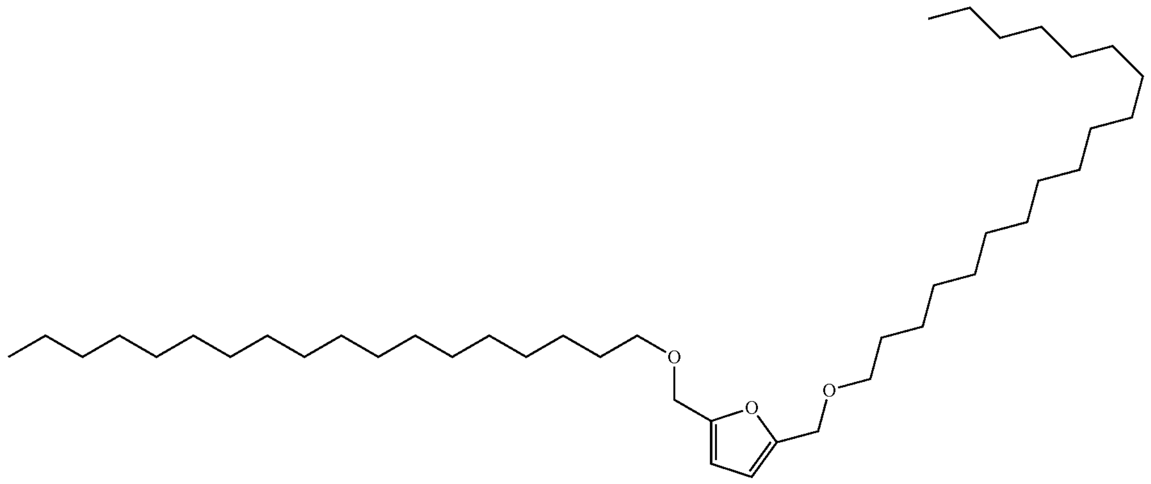

.

In yet a further embodiment, the present disclosure provides a method of preparing a mono-ether involving: contacting bHMTHFs with a Brønsted base and 1 or less molar equivalents of an alkyl-X species according to the following:

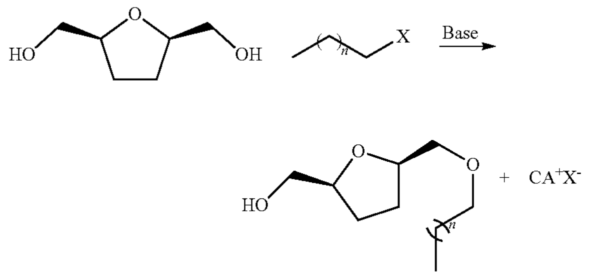

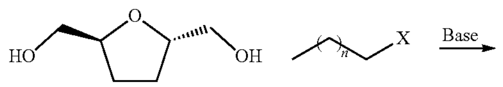

-continued

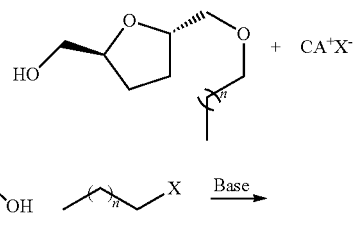

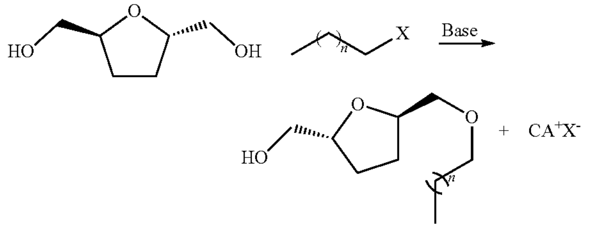

wherein: "X" is the nucleofuge, "n" is an integer from 5 to 25, and "CA" is a conjugate acid. The resultant mono-ether of bHMTHF can be, for example, at least one of the following compounds:

a. ((2S,5R)-5-((hexyloxy)methyl)tetrahydrofuran-2-yl) methanol
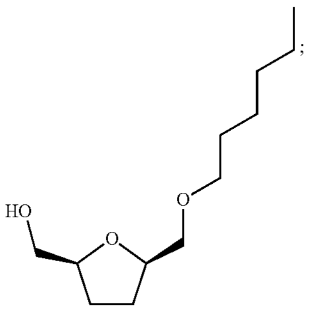
b. ((2S,5S)-5-((hexyloxy)methyl)tetrahydrofuran-2-yl) methanol
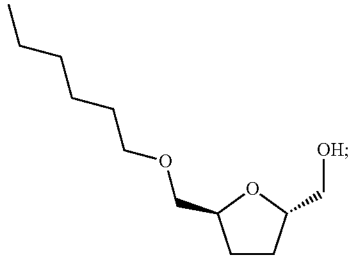
c. ((2S,5S)-5-((hexyloxy)methyl)tetrahydrofuran-2-yl) methanol
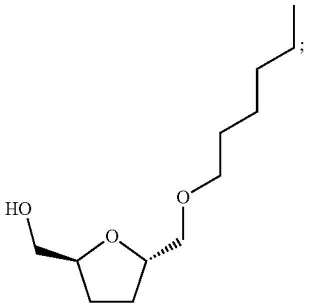
d. ((2S,5R)-5-((dodecyloxy)methyl)tetrahydrofuran-2-yl) methanol
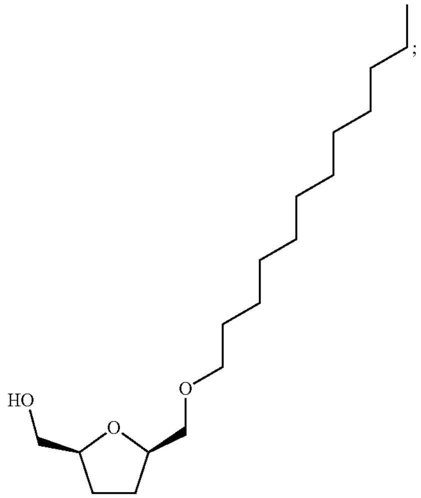 [SMILES: CCCCCCCCCCCCOC[C@H]1CC[C@@H](CO)O1]
e. ((2S,5S)-5-((dodecyloxy)methyl)tetrahydrofuran-2-yl) methanol
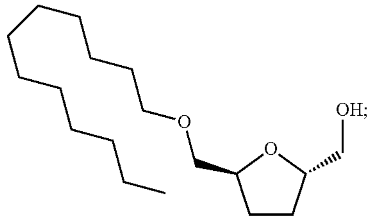 [SMILES: CCCCCCCCCCCCOC[C@@H]1CC[C@@H](CO)O1]
f. ((2S,5S)-5-((dodecyloxy)methyl)tetrahydrofuran-2-yl) methanol
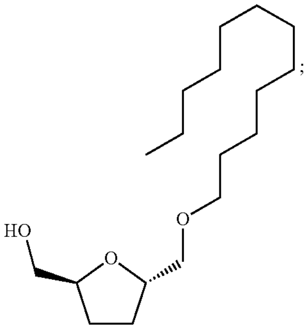 [SMILES: CCCCCCCCCCCCOC[C@@H]1CC[C@@H](CO)O1]

g. ((2S,5R)-5-((octadecyloxy)methyl)tetrahydrofuran-2-yl)methanol

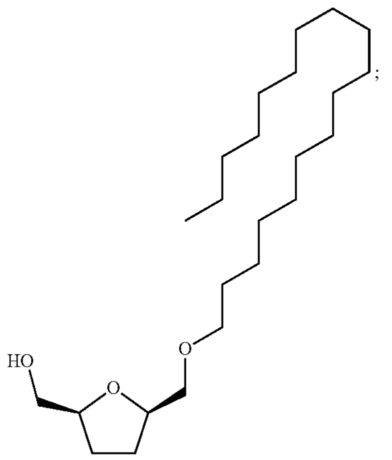 [SMILES: CCCCCCCCCCCCCCCCCCOC[C@H]1CC[C@@H](CO)O1]

h. ((2S,5S)-5-((octadecyloxy)methyl)tetrahydrofuran-2-yl)methanol

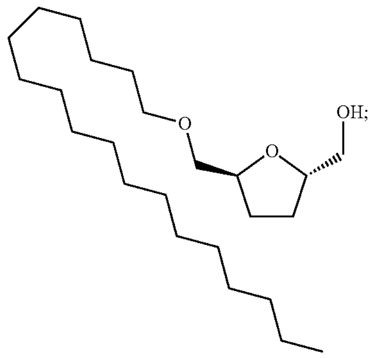 [SMILES: CCCCCCCCCCCCCCCCCCOC[C@@H]1CC[C@@H](CO)O1]

i. ((2S,5S)-5-((octadecyloxy)methyl)tetrahydrofuran-2-yl)methanol

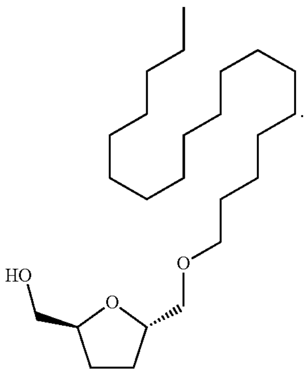 [SMILES: CCCCCCCCCCCCCCCCCCOC[C@@H]1CC[C@@H](CO)O1]

In an embodiment for preparing di-ethers, the method involves: contacting bHMTHFs with a Brønsted base and a minimum of two molar equivalents of an alkyl-X species according to the following:

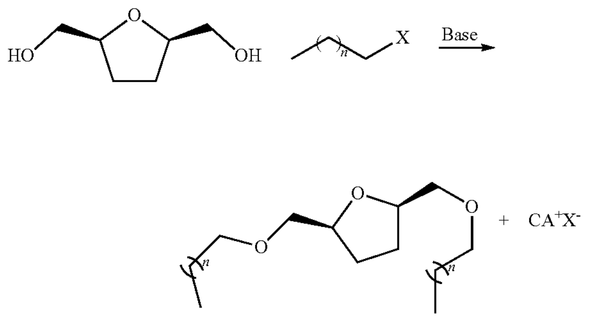

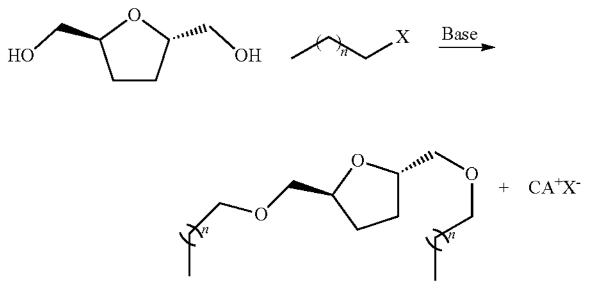

wherein: "X" is the nucleofuge, "n" is an integer from 5 to 25, and "CA" is a conjugate acid. The resultant di-ethers of bHMTHF can be, for instance, at least one of the following compounds:

a. (2R,5S)-2,5-bis((hexyloxy)methyl)tetrahydrofuran

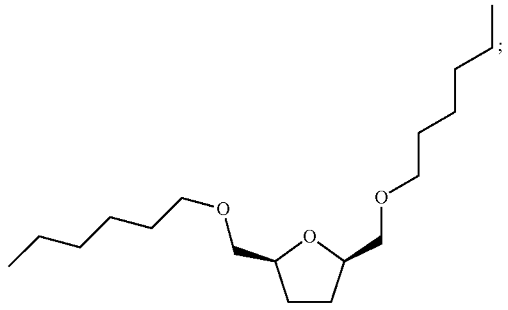 [SMILES: CCCCCCOC[C@H]1CC[C@@H](COCCCCCC)O1]

b. (2S,5S)-2,5-bis((hexyloxy)methyl)tetrahydrofuran

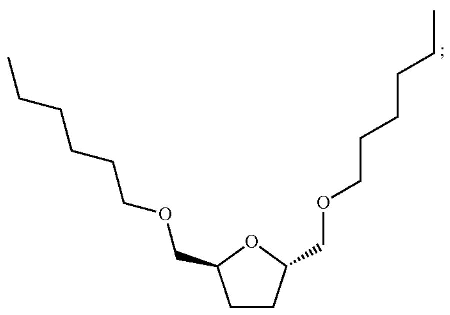 [SMILES: CCCCCCOC[C@@H]1CC[C@@H](COCCCCCC)O1]

c. (2R,5S)-2,5-bis((dodecyloxy)methyl)tetrahydrofuran

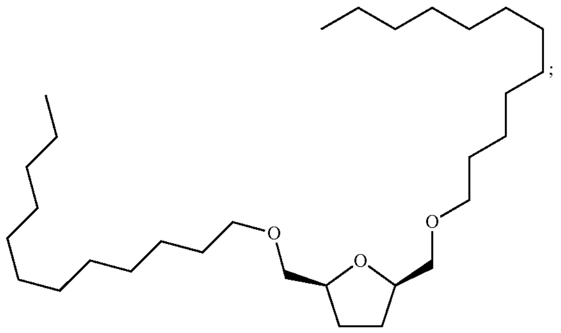 [SMILES: CCCCCCCCCCCCOC[C@H]1CC[C@@H](COCCCCCCCCCCCC)O1]

d. (2S,5S)-2,5-bis((dodecyloxy)methyl)tetrahydrofuran

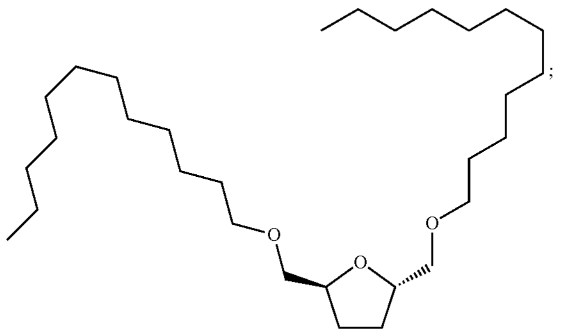 [SMILES: CCCCCCCCCCCCOC[C@@H]1CC[C@@H](COCCCCCCCCCCCC)O1]

e. (2R,5S)-2,5-bis((octadecyloxy)methyl)tetrahydrofuran

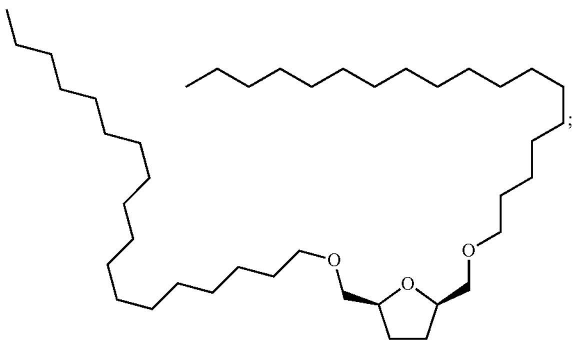 [SMILES: CCCCCCCCCCCCCCCCCCOC[C@H]1CC[C@@H](COCCCCCCCCCCCCCCCCCC)O1]

f. (2S,5S)-2,5-bis((octadecyloxy)methyl)tetrahydrofuran

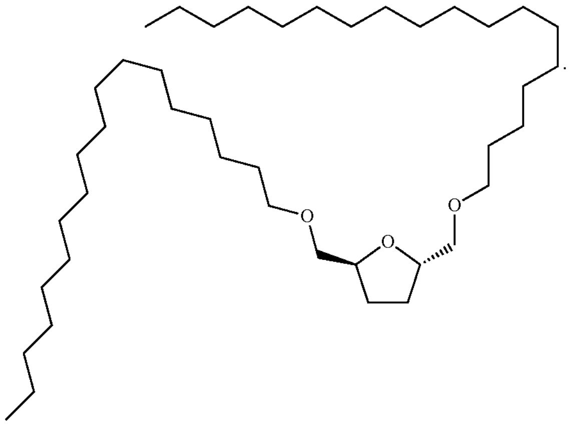 [SMILES: CCCCCCCCCCCCCCCCCCOC[C@@H]1CC[C@@H](COCCCCCCCCCCCCCCCCCC)O1]

Additionally, in another aspect, the present disclosure pertains to derivative compounds from the linear mono-ethers of FDM and bHMTHF described above and methods for making the derivatives. These derivative compounds are amphiphilic variants of the mono-ethers and are valued as precursors or plausible bio-based surfactants, dispersants, and/or hydrophiles.

Additional features and advantages of the present process will be disclosed in the following detailed description. It is understood that both the foregoing summary and the following detailed description and examples are merely representative of the invention, and are intended to provide an overview for understanding the invention as claimed.

DETAILED DESCRIPTION OF THE INVENTION

Section I.—Description

The present synthetic processes opens a pathway for direct preparation of linear alkyl ethers from the glycols FDM and/or bHMTHF, molecules that arise from the reduction of fructose derived 5-(hydroxymethyl)furfural (HMF) under mild conditions, and their derivative chemical compounds. (Although not necessary, in certain embodiments, the process may also include either first partially reducing HMF to FDM or fully reducing HMF to bHMTHFs in hydrogenation steps prior to selective etherification according to the present reaction process described herein.) The alkyl ethers, in turn, are valuable precursors with bio-based amphiphilic properties that can be used in surfactants, dispersants, and plasticizers.

In general, the process for generating alkyl ethers can be implemented in a single reaction step, in which the FDM or bHMTHF glycol is reacted with either one or two equivalents of a halogenated or sulfonated (leaving group) alkane, depending respectively on whether a mono- or di-ether product is desired. A hindered Brønsted base with a minimum pKa of about 10, preferably about 16, or an unhindered Brønsted base having a difference in pKa (ΔpKa) of ≥15 relative to the pKa of a hydroxyl group of either the FDM or bHMTHF is used to deprotonate the —OH moieties of the glycols, enhancing their nucleophilicities by several orders of magnitude towards nucleofuge displacement. (It is believed that with a pronounced difference in the pKa between the Brønsted base and the —OH moieties of the FDM and/or bHMTHF glycols, the Brønsted base should have a limited propensity to react with an alkyl halide or sulfonate in a nucleophilic substitution and/or elimination.) A polar aprotic organic solvent with a dielectric constant of ≥10, preferably ≥30, is employed to augment the basicity of the Brønsted base via charge separation capacities. Typically, the reaction is conducted at a temperature in a range from about −20° C. to about 100° C., over a period of about 2 or 3 hours. In some other iterations the time may involve about 4 or 8 hours up to about 12 or 24 hours, as conditions may dictate.

A. Brønsted Bases

As stated, the Brønsted base in the reaction serves to deprotonate the —OH moieties of the glycols. This helps to enhance the corresponding nucleophilicity of the glycols example, hydroxides (e.g., methoxide, ethoxide, t-butoxide, and benzyl oxide). Preferably, Brønsted bases having pKa's ≥30 are used, as the equilibrium for deprotonation favors generation of the desired products, such as illustrated in the examples in Scheme 3. Certain favored Brønsted bases of this type may include, for example, metallic hydrides (e.g., lithium, potassium, or sodium hydrides); metal amides (e.g., potassium or sodium amides); lithium diisopropylamide (LDA); organometallic compounds (e.g., alkyl lithium (e.g., methyl-lithium, n-butyl-lithium, or phenyl-lithium), alkyl magnesium, or alkyl cuprate) and Grignard reagents (e.g., ethylmagnesium bromide, phenylmagnesium bromide). In contrast, certain disfavored Brønsted bases may include, for example, nitrogen-centered bases (e.g., tertiary amines, aryl amine), because of low-pKa-favoring reactants and nucleophilic propensities.

Scheme 3. - Equilibrium constants for various Brønsted based deprotonations of FDM: a) with potassium hydroxide; b) with potassium t-butoxide; c) with sodium hydride.

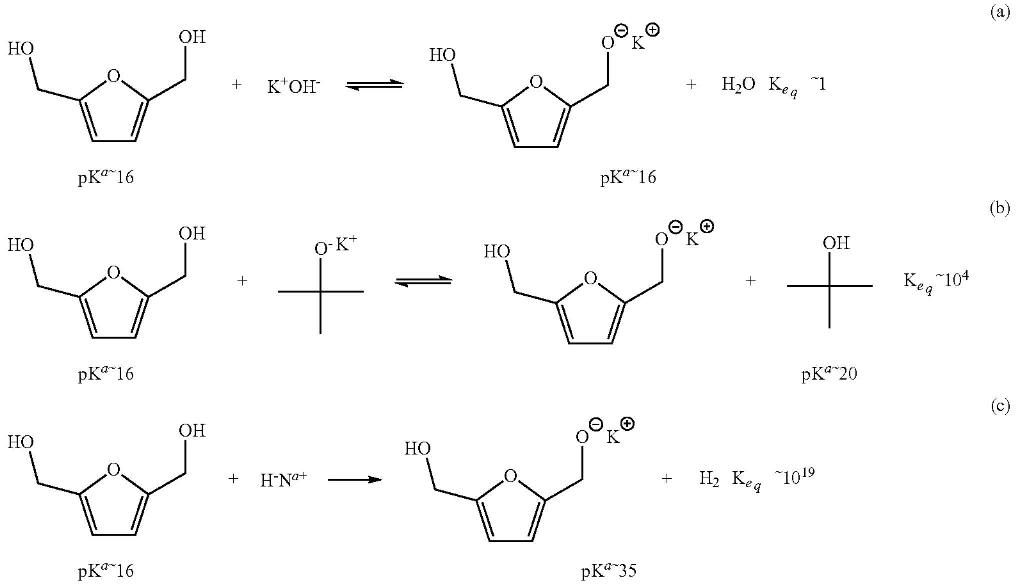

FDM and bHMTHF by about at least 6 or more orders of magnitude (e.g., 8-10-12) and drives halide/sulfonate displacement on the alkyl reagent. The relative strength of a Brønsted base used in the reaction is of essence in furnishing high conversions of the glycols to, in particular, mono-alkyl ethers.

For some Brønsted bases that have a pKa of at least 10 to about 15, the synthesis reaction usually requires the addition of heat to proceed; hence, reaction temperatures of about 45° C.-50° C. or greater. This, however, can increase the risk of generating side-products (e.g., product of Brønsted base-nucleophilic substitution with the alkyl halide/sulfonate and/or alkenes formed from Brønsted base-mediated elimination of the alkyl halide/sulfonate) and reducing the overall yield of the desired synthesis. To minimize the generation of side products and counteract this phenomenon, a Brønsted base that has a pKa of at least ~16, typically ≥20, is favored according to certain embodiments of the present process. Brønsted bases with a greater pKa more easily reacts with the —OH moieties of the glycols. This is an advantage that helps one operate effectively the reaction at about ambient room temperatures (e.g., ~18° C.-22° C.) or lower temperatures. Some suitable Brønsted bases may include, for Reaction (a) shows when using a Brønsted base having a pKa ~16, the reaction tends to be at equilibrium between product and reactants. In Reaction (b), when using a Brønsted base having a pKa ~20, the reaction tend to favor the product more, whereas in Reaction (c) when using a Brønsted base having pKa ≥30, the reaction is driven completely towards product formation.

Another factor according to an embodiment of the present invention is to employ a Brønsted base that has molecular bulk. Propitiously, the bulky Brønsted base impedes undesired nucleophilic substitutions of the Brønsted base with the alkyl halide/sulfonate. Hence, a more sterically hindered Brønsted base enhances more effectively the reaction to produce predominantly the ether product. Scheme 4 illustrates this feature. As an example, reaction (a) using an unhindered Brønsted base tends to make a mixed product of both straight-chain and FDM ethers. In contrast, reaction (b) with a more bulky, hindered Brønsted base generates the FDM ethers alone.

Scheme 4. - Examples of Brønsted bases: a) unhindered, nucleophilic base, with sodium methoxide; b) hindered, non-nucleophilic base with potassium t-butoxide.

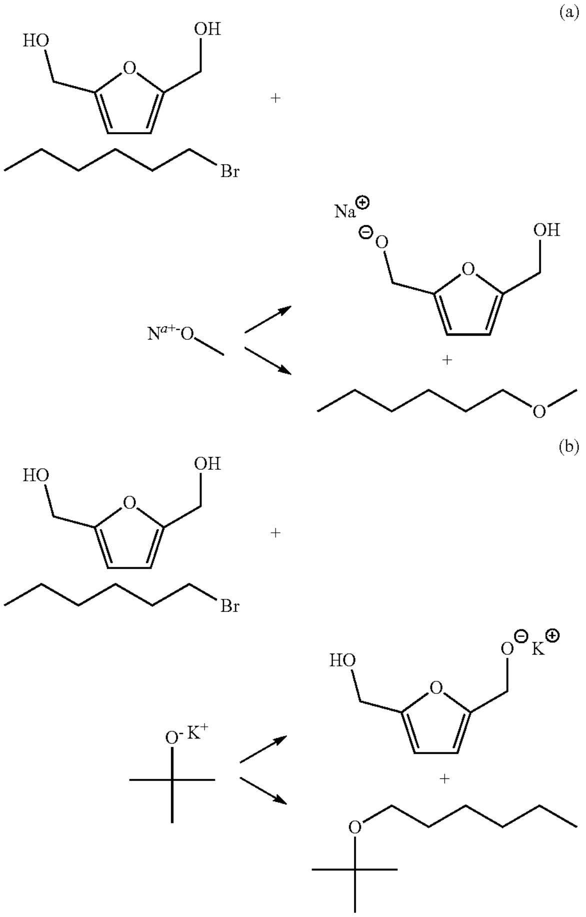

B. Alkyl Halides and Sulfonates

The etherification reaction of the present description can be characterized as a base-mediated, second order substitution reaction between a glycol and activated alkane. To achieve satisfactory yields of the desired ether in a polar aprotic organic solvent most expeditiously, the leaving group affixed to the alkane should exhibit favorable nucleofugal properties. Some species in this context can be, for example, halides (e.g., Cl, Br, I) and sulfonates (e.g., —OTf, —OTs, —OMs). Typically, one can conduct the reaction using straight-chain alkyl halides or sulfonates of 5 to 25 carbons in length. In some reactions, for instance, the alkyl chain lengths may range from about 5 or 8 to about 16 or 18 carbons, or about 6 or 10 to about 20 or 22 carbons (e.g., $C_8$-$C_{18}$; $C_5$-$C_{15}$; $C_6$-$C_{12}$), or any iteration therein between.

One can use a variety of sulfonates, including but not limited to, mesylate (methanesulfonate), $CH_3SO_2O$— 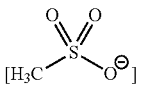 (—OMs);

triflate (trifluoromethanesulfonate), $CF_3SO_2O$— 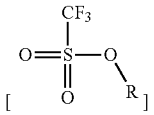 (—OTfs);

tosylate (p-toluenesulfonate), $CH_3C_6H_4SO_2O$— 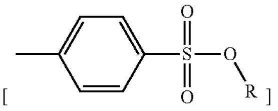 (—OTs);

esylate (ethanesulfonate), $C_2H_5SO_2O$— 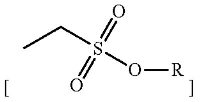 (—OEs);

besylate (benzenesulfonate), $C_6H_5SO_2O$— 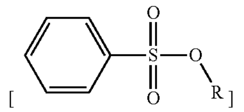 (—OBs), and other alkyl and aryl sulfonates without limitation.

As halides, such as bromides, and alcohols are more economically accessible commercial alkane sources, they may be favored for larger scale, industrial uses according to some embodiments. In a situation in which an alkyl halide is unavailable or prohibitively expensive, but the corresponding alcohol available, one may substitute the alcohol for the corresponding sulfonate through a simple sulfonation reaction.

In certain embodiments, the sulfonate is preferably a triflate because it is a powerful leaving group. This reaction exhibits relatively fast kinetics and generates an activated triflic complex. The reaction is usually conducted at a low temperature, less than 0° C. (e.g., typically about −10° C. or −12° C. to about −20° C. or −25° C.), to control the reaction kinetics more easily. This reaction is essentially irreversible, as the liberated triflate is entirely non-nucleophilic. The triflic complex then reacts readily with the FDM or bHMTHF, forming respectively a FDM or bHMTHF-triflate with concomitant release and protonation of a nucleophilic base (e.g., pyrimidine, dimethyl-aminopyridine, imidazole, pyrrolidine, and morpholine).

The tosylate, mesylate, brosylate, benzenesulfonate, ethylsulfonate or other sulfonate species can be as effective as triflate in imparting leaving groups, and manifesting overall yields that were commensurate with that achieved with triflate. But, these other sulfonates tend to react more slowly in comparison to the triflate. To compensate for this, operations at higher temperatures are typically needed for better yields when using these other species.

Often the conversion can be performed sequentially in a single reaction vessel, prior to executing a displacement reaction with a glycol, such as demonstrated in Scheme 5.

Scheme 5. - Single-vessel sequential sulfonation, displacement reaction between FDM and dodecanol.

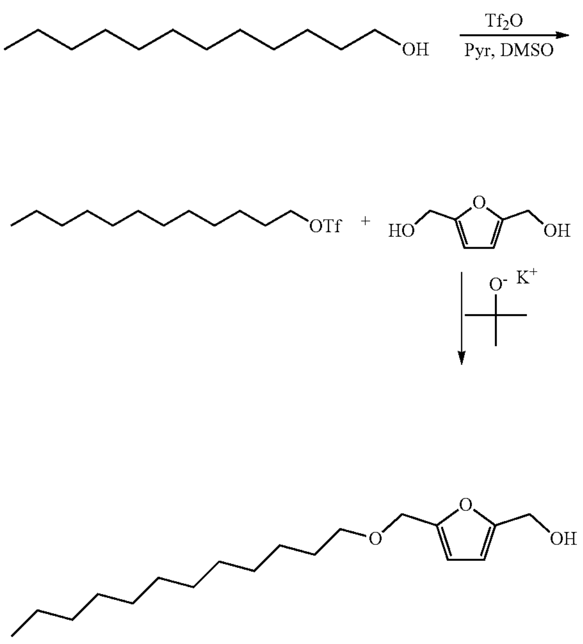

-continued

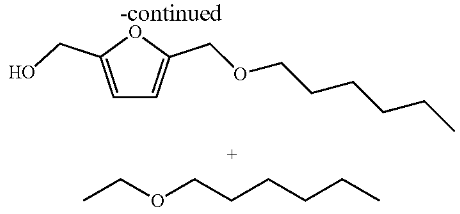

C. Organic Solvents

In the present synthesis process, aprotic solvents are used, as they contain no functionality labile to covalent modifications with the glycol, alkyl halide/sulfonate and Brønsted base of the title reaction, and thus do not interfere with the Sn2-driven process. Furthermore, polar aprotic solvents (i.e., solvents with a permanent dipole moment but without the ability to act as hydrogen bond donors) are favored in the present etherification reactions. Polar aprotic solvents adequately dissolve the glycols and the alkyl halide/sulfonate, a feature for an efficient reaction to occur. The function is dissimilar to apolar solvents like hexane or benzene, which lack the ability to effectuate charge separation of the anionic Brønsted base from its cation counterpart, rendering it inactive. Also, polar aprotic solvents tend not to react with the alkyl halide/sulfonate (cf., Scheme 6, ethanol, a polar protic solvent, which can generate undesired side products).

Scheme 6. - Solvent etherification potential with ethanol, a polar protic solvent.

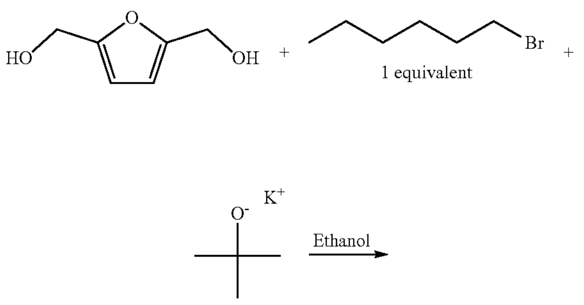

In aprotic solvents a greater dielectric constant can help prevent the solvent from reacting with the primary reagents, hence minimizing formation of side-products. The reactions of the present synthesis process are conducted in solvents with a relative permittivity $\geq \in_r$ 25, typically about 30 or 35. For example, DMSO and DMF exhibit relatively high dielectric constants (e.g., ~30 or 32). Other solvents with high boiling points and dielectric constants, such as NMP and DMA, are effective in cyanide for sulfonate displacement reactions. The reaction to derivatize FDM or bHMTHF with a sulfonate is performed in a solution of solvent having a boiling point ≥110° C.

Some common polar aprotic solvents that are amenable to this process are dimethylformamide (DMF), dimethylsulfoxide (DMSO), dimethylacetamide (DMA), N-methylpyrrolidone (NMP), hexamethylphosphoramide (HMPA), acetone, acetonitrile (ACN), nitromethane, sulfolane, tetrahydrofuran (THF), 1,4-dioxane, and ethyl acetate.

A further consideration when using polar aprotic solvent in the etherification process is to amply charge separate the Brønsted base so that the glycol —OH moieties can be deprotonated. A reflection of the power to charge separate is the permittivity of dielectric constant, represented by ∈ (no units), with the larger number signifying a greater capacity to sequester the ions. In general, e>20 is the advantageous for effective charge separation, with exceptions being THF (∈=7.58) and 1,4-dioxane (∈=2.21) whose oxygen atoms can coordinate with cations captodatively. The preferred ∈ is >30. Examples of polar aprotic solvents with propitious ∈ are DMSO (∈=46.7), sulfolane (∈=43.3), DMA (∈=37.8), acetonitrile (∈=37.5), DMF (∈=36.7), nitromethane (∈=35.9), NMP (∈=32.0), HMPA (∈=30.0), acetone (∈=20.0).

D. Reaction Temperature

One of the advantages of the present synthesis process is that it can be operated in a relatively mild temperature range, and under less harsh conditions than some other conventional reaction processes. Depending on the particular Brønsted base, the reaction temperatures can span between about −25° C. or −20° C. to about 80° C. or 100° C. Typically, the reaction temperature is in a range from about −12° C. or −7° C. to about 65° C. or 70° C., more typically from about −10° C. or −5° C. to about 40° C. or 50° C. In certain embodiments, preferred temperatures may range from about −10° C. or −8° C. to about 25° C. or 30° C., or about −3° C. or 0° C. to about 32° C. or 35° C., inclusive. Preferably, the reaction can be performed at or below ambient room temperatures (e.g., ≤about 22° C. or 25° C.). Because of a potential or tendency to generate olefins from base-mediated elimination of an alkyl halide/sulfonate at elevated temperatures, and potential slow reaction kinetics when uses certain Brønsted bases (Scheme 7), temperature control for the present selective etherification is an important factor. (As aforementioned, a Brønsted base with a pKa lower than 16, which designates that of the —OH moieties of FDM and bHMTHF, tends to favor the reactants at equilibrium; hence the reaction is performed at an elevated temperature (e.g., >25° C., 35° C., or 40° C.) to drive the etherification, albeit with a greater risk of forming side products (olefins).)

Scheme 7. - Reaction temperature profiles with a) potassium t-butoxide, and b) sodium hydride as Brønsted bases.

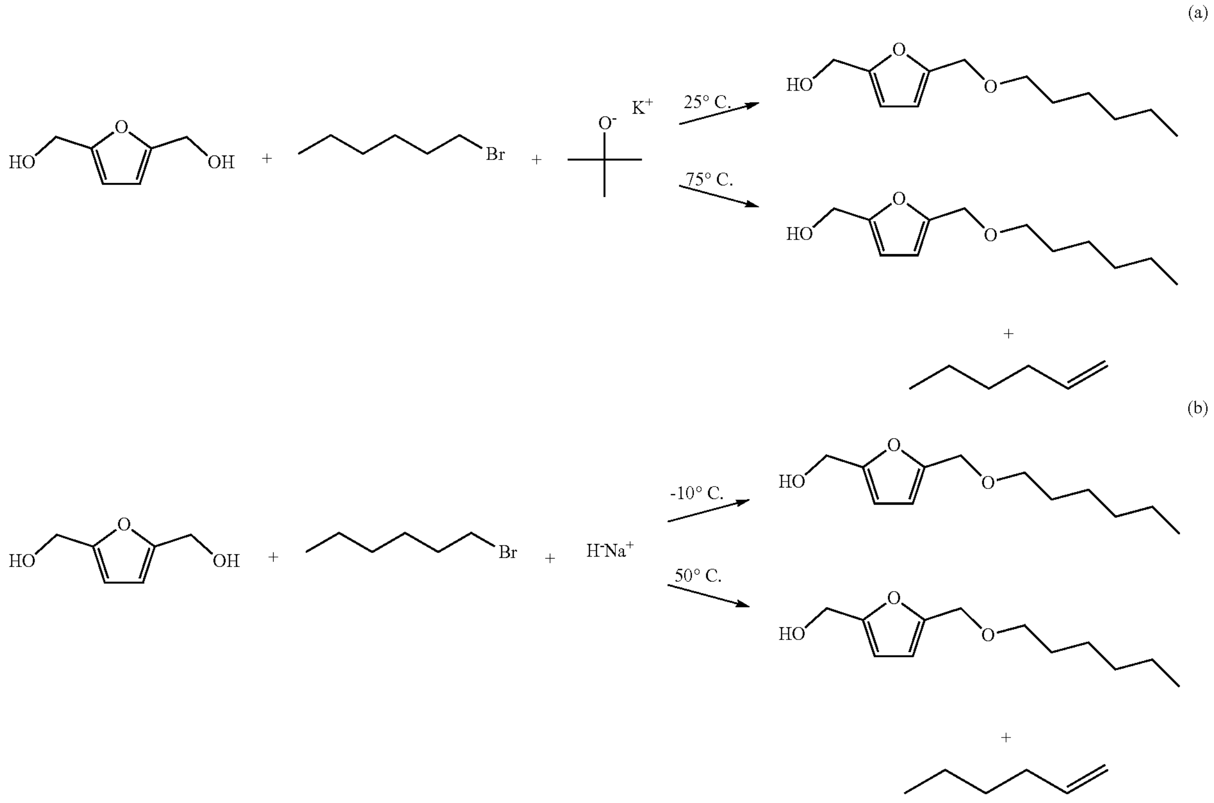

E. Derivatives

In another aspect, various amphiphilic compounds can be synthesized from FDM or bHMTHF ethers as a starting or precursor material. Such derivative materials can be useful as substitutes for existing compounds or new chemical building blocks in surfactant, dispersant, plasticizer or a component in other applications. The derivative amphiphilic compounds can be prepared according to various chemical reactions available for organic synthesis. Preparations of some representative derivative compounds are further described in the accompanying examples below.

The methods may include: reacting either a mono-ether of bHMTHF or FDM with: a) chlorosulfonic acid to generate a sulfate, or b) trifluoromethanesulfonic anhydride to generate a trifluoromethanesulfonate, respectively, of each glycol species. For the derivatives of bHMTHF mono-ethers, a sulfate product can be, for example, at least one of the following compounds:

a. ((2S,5R)-5-((hexyloxy)methyl)tetrahydrofuran-2-yl) methyl hydrogen sulfate

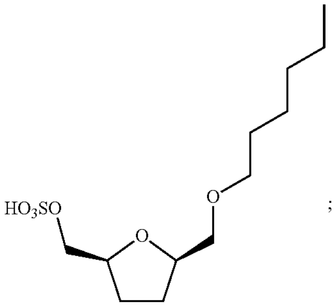

;

b. ((2S,5S)-5-((hexyloxy)methyl)tetrahydrofuran-2-yl) methyl hydrogen sulfate

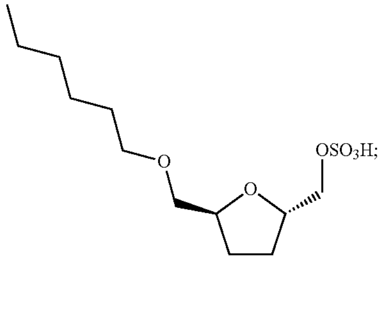

c. ((2S,5S)-5-((hexyloxy)methyl)tetrahydrofuran-2-yl) methyl hydrogen sulfate

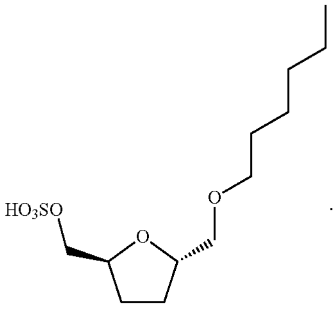

.

Alternatively, a trifluoromethanesulfonated mono-ether generated from the bHMTHF mono-ether can be, for example, at least one of the following compounds:

a. ((2S,5R)-5-((dodecyloxy)methyl)tetrahydrofuran-2-yl) methyl trifluoromethanesulfonate

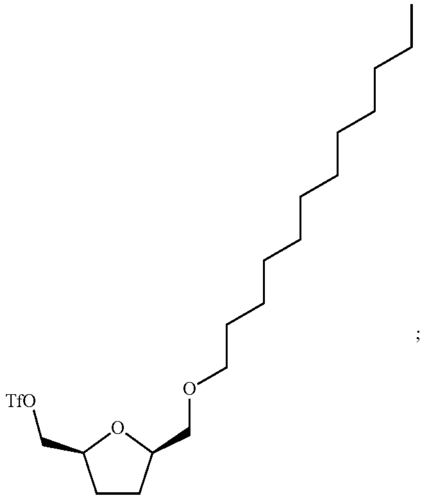 [SMILES: CCCCCCCCCCCCOC[C@H]1CC[C@@H](COS(=O)(=O)C(F)(F)F)O1]

;

b. ((2S,5S)-5-((dodecyloxy)methyl)tetrahydrofuran-2-yl) methyl trifluoromethanesulfonate

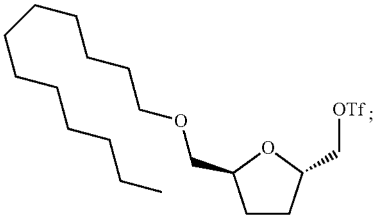 [SMILES: CCCCCCCCCCCCOC[C@@H]1CC[C@@H](COS(=O)(=O)C(F)(F)F)O1]

;

c. ((2S,5S)-5-((dodecyloxy)methyl)tetrahydrofuran-2-yl) methyl trifluoromethanesulfonate

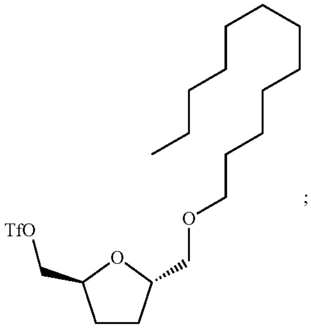 [SMILES: CCCCCCCCCCCCOC[C@@H]1CC[C@@H](COS(=O)(=O)C(F)(F)F)O1]

;

d. ((2S,5R)-5-((octadecyloxy)methyl)tetrahydrofuran-2-yl)methyl trifluoromethanesulfonate

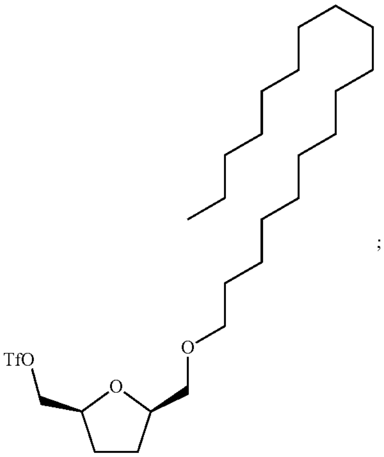 [SMILES: CCCCCCCCCCCCCCCCCCOC[C@H]1CC[C@@H](COS(=O)(=O)C(F)(F)F)O1]

;

e. ((2S,5S)-5-((octadecyloxy)methyl)tetrahydrofuran-2-yl)methyl trifluoromethanesulfonate

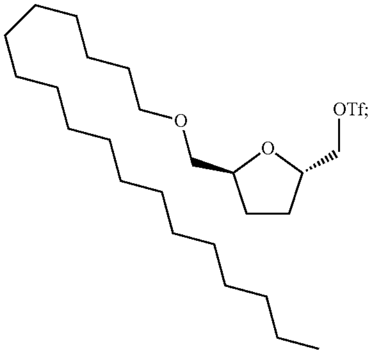 [SMILES: CCCCCCCCCCCCCCCCCCOC[C@@H]1CC[C@@H](COS(=O)(=O)C(F)(F)F)O1]

;

f. ((2S,5S)-5-((octadecyloxy)methyl)tetrahydrofuran-2-yl)methyl trifluoromethanesulfonate

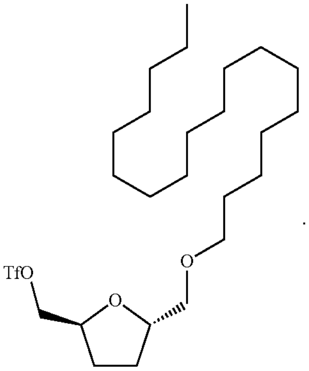 [SMILES: CCCCCCCCCCCCCCCCCCOC[C@@H]1CC[C@@H](COS(=O)(=O)C(F)(F)F)O1]

.

The process may further involve generating an ethoxyethanolamine derivative of the bHMTHF mono-ether sulfonate compound by substitution of a sulfonate group with an ethanolamine. The resultant ethoxyethanolamine prepared can be, for instance, at least one of the following compounds:

a. 2-(2-((((2S,5R)-5-((dodecyloxy)methyl)tetrahydrofuran-2-yl)methyl)amino)ethoxy)-ethanol

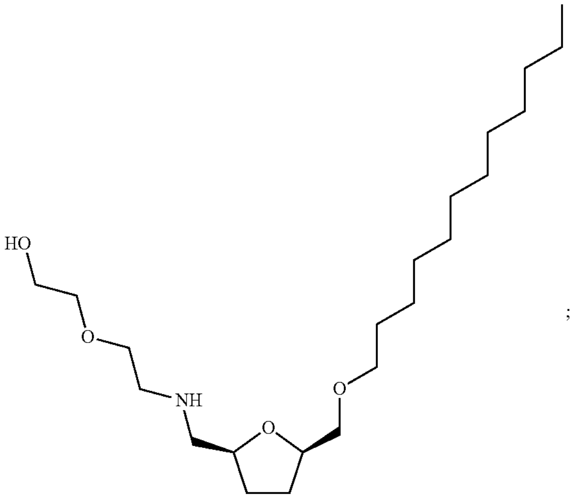 [SMILES: CCCCCCCCCCCCOC[C@H]1CC[C@@H](CNCCOCCO)O1]

;

b. 2-(2-((((2S,5S)-5-((dodecyloxy)methyl)tetrahydrofuran-2-yl)methyl)amino)ethoxy)-ethanol

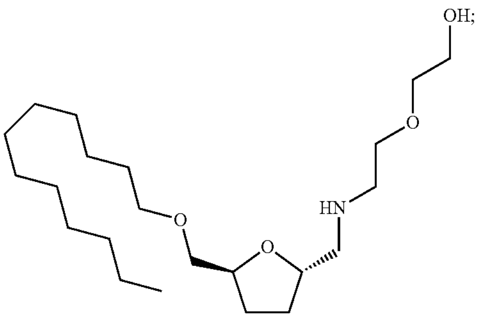 [SMILES: CCCCCCCCCCCCOC[C@@H]1CC[C@@H](CNCCOCCO)O1]

c. 2-(2-((((2S,5S)-5-((dodecyloxy)methyl)tetrahydrofuran-2-yl)methyl)amino)ethoxy)-ethanol

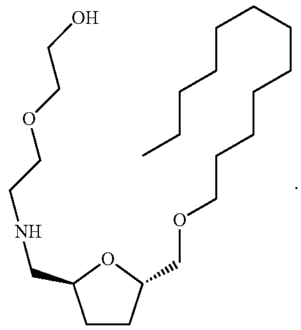 [SMILES: CCCCCCCCCCCCOC[C@@H]1CC[C@@H](CNCCOCCO)O1]

.

In an alternative embodiment, the process may further include generating a primary amine of a bHMTHF monoether by substitution of a trifluoromethanesulfonate group to form a benzyl-amine, such as one of the following:

a) N-benzyl-1-(5-((hexyloxy)methyl)furan-2-yl)methanamine

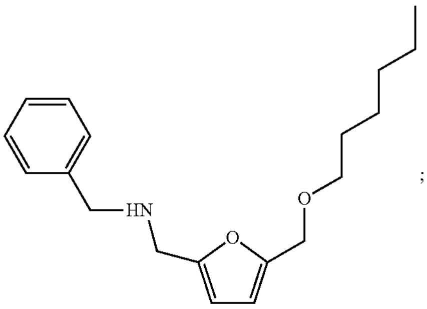 [SMILES: CCCCCCOCc1ccc(CNCc2ccccc2)o1]

;

b) N-benzyl-1-((2S,5S)-5-((octadecyloxy)methyl)tetrahydrofuran-2-yl)methanamine

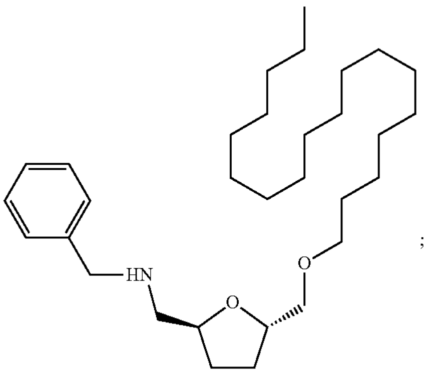 [SMILES: CCCCCCCCCCCCCCCCCCOC[C@@H]1CC[C@@H](CNCc2ccccc2)O1]

;

c) N-benzyl-1-((2S,5S)-5-((octadecyloxy)methyl)tetrahydrofuran-2-yl)methanamine

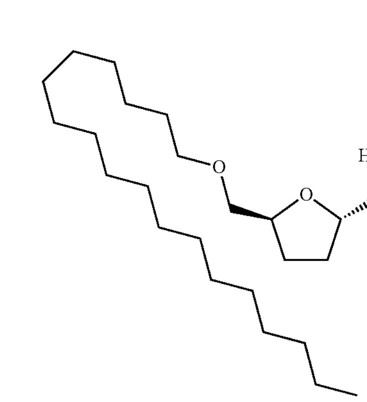

;

and d) N-benzyl-1-((2S,5R)-5-((octadecyloxy)methyl)tetrahydrofuran-2-yl)methanamine

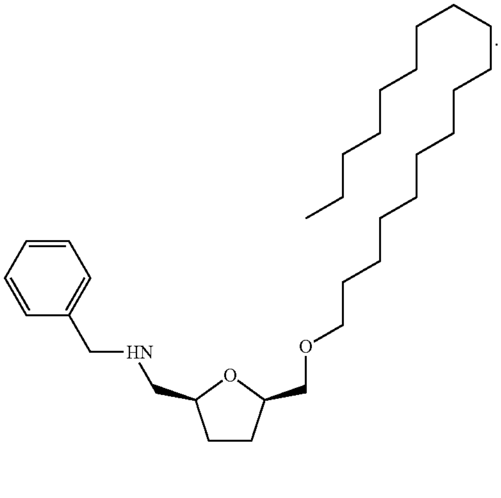 [SMILES: CCCCCCCCCCCCCCCCCCOC[C@H]1CC[C@@H](CNCc2ccccc2)O1]

.

Subsequently, one generates the primary amine by catalytic debenzylation with, for example, a palladium catalyst on carbon. The resultant primary amine can be, for instance, at least one of the following compounds:

a. ((2S,5R)-5-((octadecyloxy)methyl)tetrahydrofuran-2-yl)methanamine

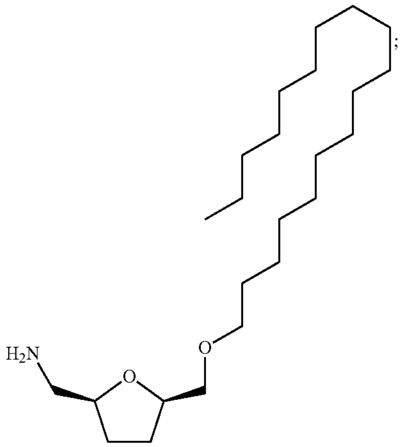 [SMILES: CCCCCCCCCCCCCCCCCCOC[C@H]1CC[C@@H](CN)O1]

;

b. ((2S,5S)-5-((octadecyloxy)methyl)tetrahydrofuran-2-yl)methanamine

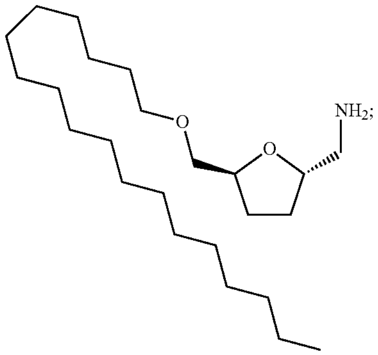 [SMILES: CCCCCCCCCCCCCCCCCCOC[C@@H]1CC[C@@H](CN)O1]

c. ((2S,5S)-5-((octadecyloxy)methyl)tetrahydrofuran-2-yl)methanamine

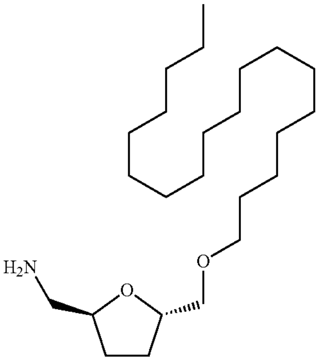

.

In another alternative embodiment, the process may further include preparing a primary ammonium salt of the bHMTHF monoether by substitution of a trifluoromethanesulfonate group followed by catalytic debenzylation and protonation by a Brønsted acid having a pKa ≤0 (e.g., HCl, HBr, HI). The resultant primary ammonium group can be, for example, at least one of the following compounds:

a. ((2S,5R)-5-((octadecyloxy)methyl)tetrahydrofuran-2-yl)methanaminium chloride

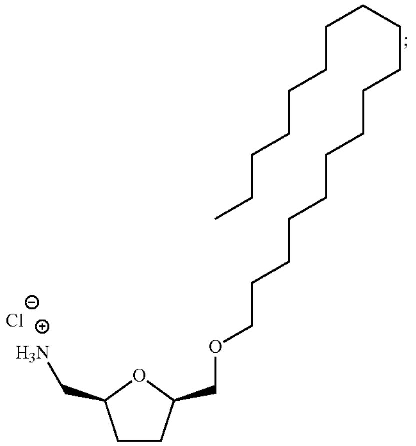

b. ((2S,5S)-5-((octadecyloxy)methyl)tetrahydrofuran-2-yl)methanaminium chloride

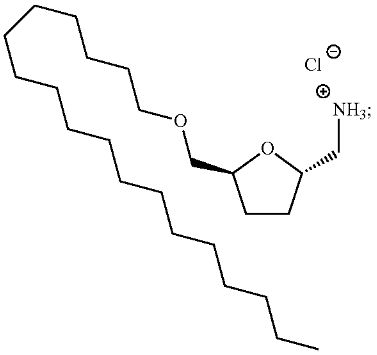

c. ((2S,5S)-5-((octadecyloxy)methyl)tetrahydrofuran-2-yl)methanaminium chloride

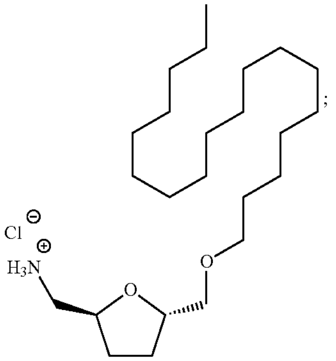 [SMILES: [Cl-] ; CCCCCCCCCCCCCCCCCCOC[C@@H]1CC[C@@H](C[NH3+])O1]

d. ((2S,5R)-5-((octadecyloxy)methyl)tetrahydrofuran-2-yl)methanaminium bromide

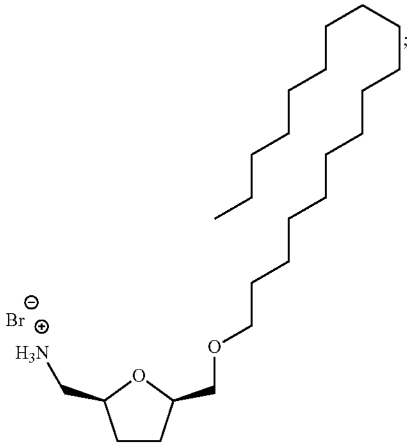

e. ((2S,5S)-5-((octadecyloxy)methyl)tetrahydrofuran-2-yl)methanaminium bromide

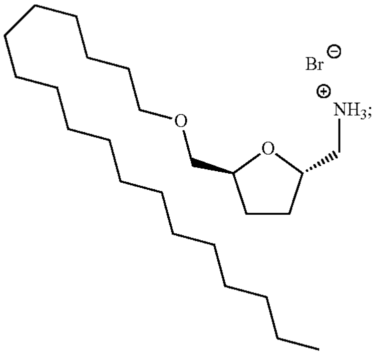

f. ((2S,5S)-5-((octadecyloxy)methyl)tetrahydrofuran-2-yl)methanaminium bromide

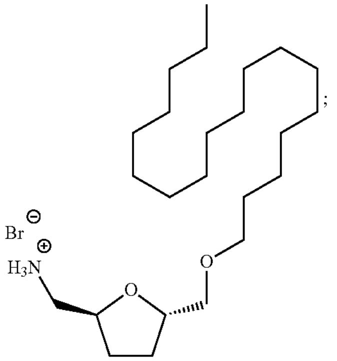

g. ((2S,5R)-5-((octadecyloxy)methyl)tetrahydrofuran-2-yl)methanaminium iodide

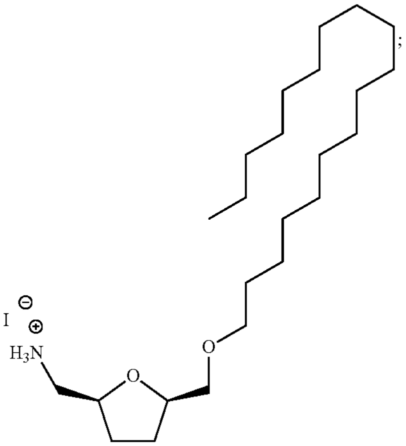 [SMILES: [I-] ; CCCCCCCCCCCCCCCCCCOC[C@H]1CC[C@@H](CN)O1]

h. ((2S,5S)-5-((octadecyloxy)methyl)tetrahydrofuran-2-yl)methanaminium iodide

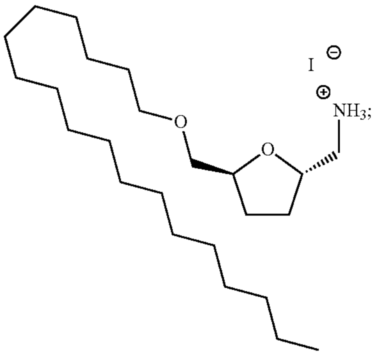

i. ((2S,5S)-5-((octadecyloxy)methyl)tetrahydrofuran-2-yl)methanaminium iodide

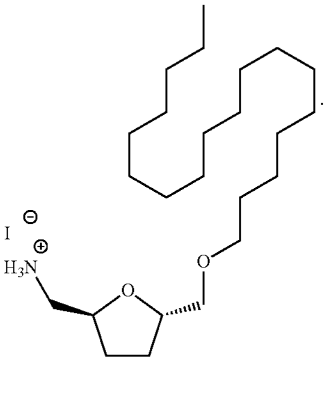 [SMILES: [I-] ; CCCCCCCCCCCCCCCCCCOC[C@@H]1CC[C@@H](C[NH3+])O1]

The salt version of the primary amine renders the molecule more amphiphilic with a polar head for cationic surfactants.

For the derivative compounds prepared from a reaction with a mono-ether of FDM, the resultant sulfate product can be for example:

a. (5-((dodecyloxy)methyl)furan-2-yl)methyl hydrogen sulfate

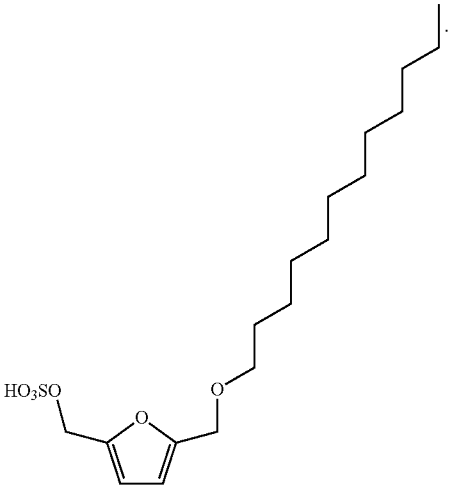

And, the resultant trifluoromethanesulfonate from FDM mono-ether can be, for example, at least one of the following structures:

a. (5-((hexyloxy)methyl)furan-2-yl)methyl trifluoromethanesulfonate

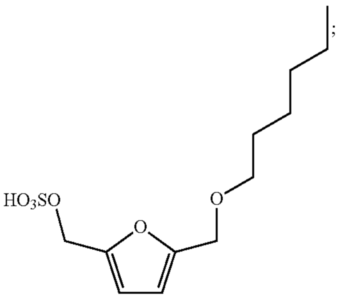

b. (5-((octadecyloxy)methyl)furan-2-yl)methyl trifluoromethanesulfonate

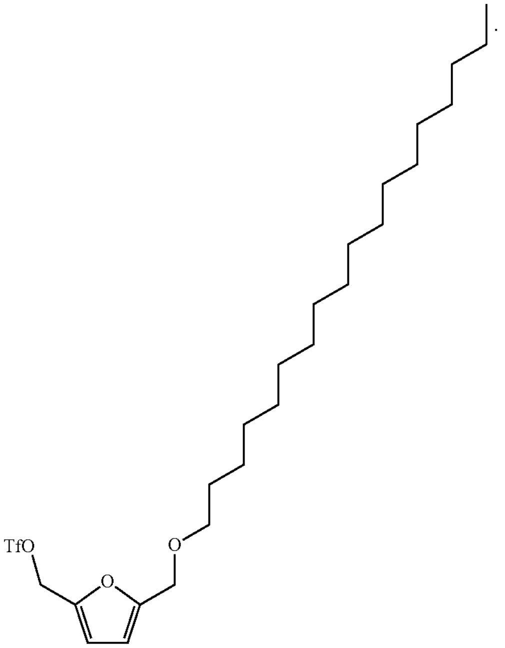 [SMILES: CCCCCCCCCCCCCCCCCCOCc1ccc(COS(=O)(=O)C(F)(F)F)o1]

Similar to the process with bHMTHF mono-ethers, the process for preparing a primary ammonium group using FDM mono-ethers also involves substitution of a trifluoromethanesulfonate group followed by catalytic debenzylation and protonation by a Brønsted acid having a pKa ≤0. The resultant aminoethylethanolamine can be, for example, the following:

a. 2-((2-(((5-((octadecyloxy)methyl)furan-2-yl)methyl)amino)ethyl)amino)-ethanol

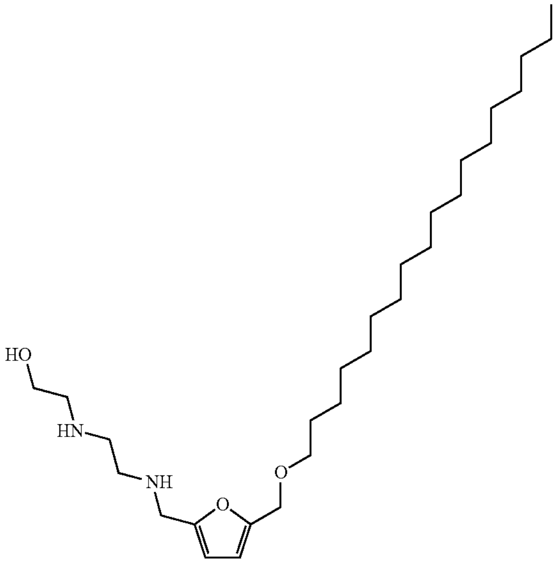 [SMILES: CCCCCCCCCCCCCCCCCCOCc1ccc(CNCCNCCO)o1]

According to another embodiment, a primary amine derivative that is prepared using FDM mono-ether as the starting material can be, for example, the following: (5-((hexyloxy)methyl)furan-2-yl)methanamine

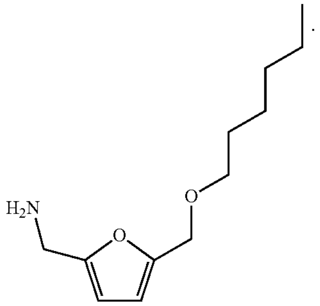

Alternatively, one can also prepare a quaternary trimethylammonium salt such as: 1-(5-((hexyloxy)methyl)furan-2-yl)-N,N,N-trimethylmethanaminium iodide

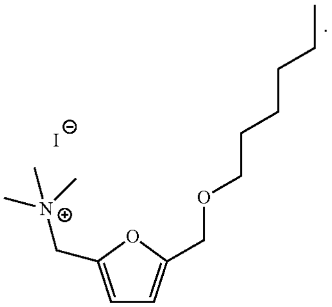 [SMILES: CCCCCCOCc1ccc(C[N+](C)(C)C)o1 ; [I-]]

Section II.—Examples

The present synthesis system is further illustrated in the following examples for making: A) bHMTHF di-ethers; B) bHMTHF mono-ethers; C) derivatives of bHMTHF mono-ethers; D) FDM di-ethers; E) FDM mono-ethers; and F) amphiphilic derivatives of FDM mono-ethers.

A. bHMTHF Diethers

Example 1: Synthesis of (2R,5S)-2,5-bis((hexyloxy)methyl)tetrahydrofuran and (2S,5S)-2,5-bis((hexyloxy)methyl)tetrahydrofuran, B

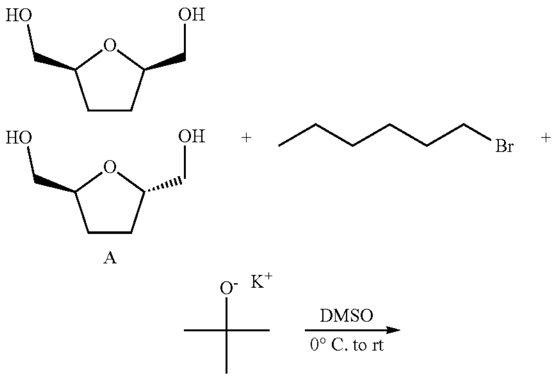

-continued

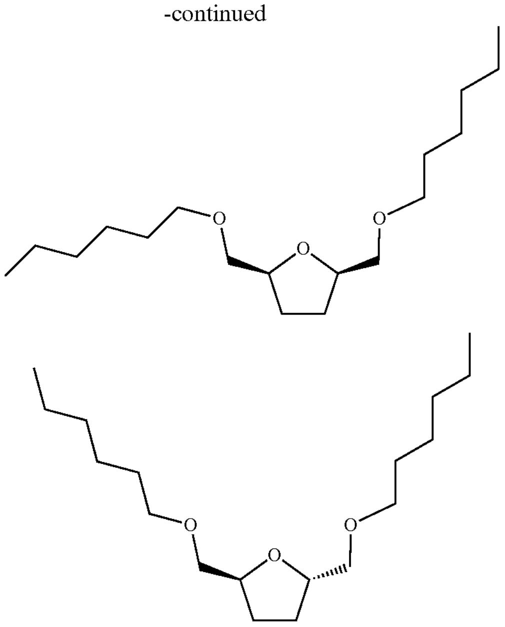

B

Experimental:

An oven dried, single neck 10 mL round bottomed flask equipped with a PTFE coated magnetic stir bar was charged with 50 mg of a 9:1 mixture of ((2R,5S)-tetrahydrofuran-2,5-diyl)dimethanol and ((2S,5S)-tetrahydrofuran-2,5-diyl)dimethanol (0.378 mmol) and 5 mL of anhydrous DMSO. The flask was then immersed in an ice-brine bath (~−10° C.) and, while stirring, 106 mg of potassium t-butoxide (0.946 mmol) added in portions and the mixture stirred for 30 minutes at this temperature. At this time, the neck was stoppered with a rubber septum and an argon gas inlet affixed via a 14" needle. While vigorously stirring and under an argon blanket, 117 μL of 1-bromohexane (0.832 mmol) was added via syringe. The mixture was then warmed to room temperature and continued to react overnight. After this time, an aliquot was removed and spotted on a silica gel TLC plate, which exhibited a single band (cerium molybdate stain) after developing in 9:1 hexanes/ethyl acetate. The signature band for A (baseline) was patently absent, suggesting this reagent had fully converted. Here, the mixture was diluted with 5 mL of water and 5 mL of methylene chloride and partitioned and the aqueous layer extracted with 3-5 mL volumes of methylene chloride. The organic phases were combined, dried with anhydrous magnesium sulfate, filtered and concentrated under vacuum. The oily residue was dissolved in a minimum amount of methylene chloride and added to 20 g of silica gel, which was then dried under vacuum, furnishing product adsorbed silica gel. This material was added to a pre-fabricated silica gel column, where flash chromatography with hexanes to 10% ethyl acetate in hexanes afforded 64 mg of a B as light yellow oil after inspissation (56% of theoretical). $^{1}H$ NMR (400 MHz, $CDCl_3$, salient peaks corresponding to the cis (meso) derivative in large excess) δ (ppm) 4.21 (m, 2H), 3.64 (m, 2H), 3.40-3.36 (m, 4H), 2.11 (m, 2H), 1.61 (m, 2H), 1.47 (t, J=6.2 Hz, 4H), 1.40 (m, 4H), 1.35-1.30 (m, 10H), 0.94 (t, J=7.0 Hz, 6H); $^{13}C$ NMR (100 MHz, $CDCl_3$ salient peaks corresponding to the cis (meso) derivative in large excess) δ (ppm) 87.1, 78.3, 68.9, 33.2, 31.2, 29.8, 25.4, 23.1, 13.3.

Example 2: Synthesis of (2R,5S)-2,5-bis((dodecyloxy)methyl)tetrahydrofuran and (2S,5S)-2,5-bis((dodecyloxy)methyl)tetrahydrofuran, B

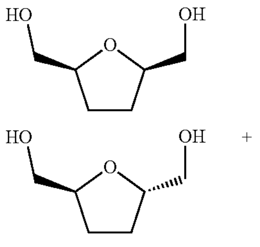

A

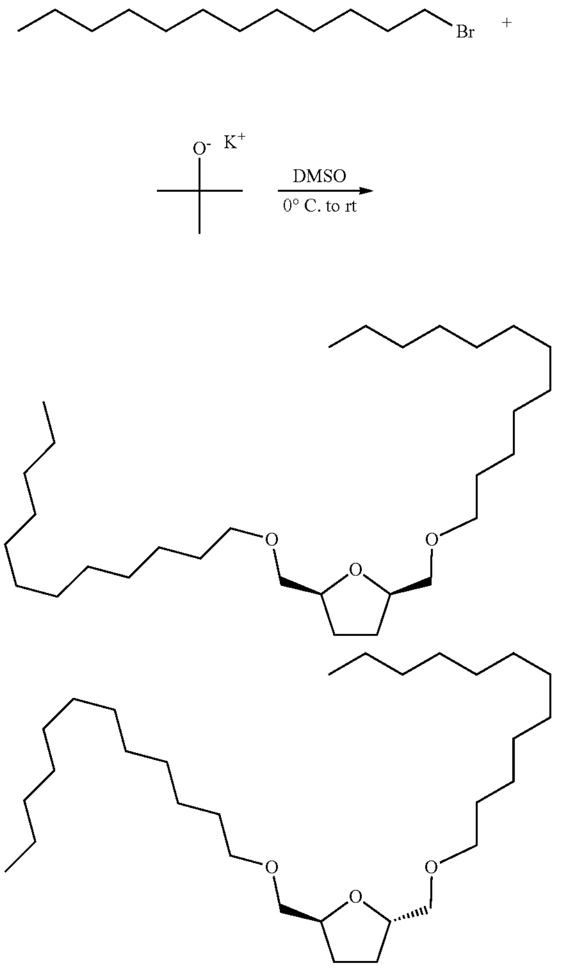

B

Experimental:

An oven dried, single neck 10 mL round bottomed flask equipped with a PTFE coated magnetic stir bar was charged with 50 mg of a 9:1 mixture of ((2R,5S)-tetrahydrofuran-2,5-diyl)dimethanol and ((2S,5S)-tetrahydrofuran-2,5-diyl)dimethanol (0.378 mmol) and 5 mL of anhydrous DMSO. The flask was then immersed in an ice-brine bath (~−10° C.) and, while stirring, 106 mg of potassium t-butoxide (0.946 mmol) added in portions and the mixture stirred for 30 minutes at this temperature. At this time, the neck was stoppered with a rubber septum and an argon gas inlet affixed via a 14" needle. While vigorously stirring and under an argon blanket, 200 μL of 1-bromododecane (0.832 mmol) was added via syringe. The mixture was then warmed to room temperature and continued to react overnight. After this time, an aliquot was removed and spotted on a silica gel TLC plate, which exhibited a single band (cerium molybdate stain) after developing in 10:1 hexanes/ethyl acetate. The signature band for A (baseline) was noticeably absent, suggesting this reagent had fully converted. Here, the mixture was diluted with 5 mL of water and 5 mL of methylene chloride and partitioned and the aqueous layer extracted with 3-5 mL volumes of methylene chloride. The organic phases were combined, dried with anhydrous magnesium sulfate, filtered and concentrated under vacuum. The oily residue was dissolved in a minimum amount of methylene chloride and added to 20 g of silica gel, which was then dried under vacuum, furnishing product adsorbed silica gel. This material was added to a pre-fabricated silica gel column, where flash chromatography with hexanes to 7% ethyl acetate in hexanes afforded 118 mg of a B as a beige solid after concentration (65% of theoretical). $^{1}H$ NMR (400 MHz, $CDCl_3$, salient peaks corresponding to the cis (meso) derivative in large excess) δ (ppm) 4.20 (m, 2H), 3.63 (m, 2H), 3.41-3.38 (m, 4H), 2.09 (m, 2H), 1.59 (m, 2H), 1.49 (t, J=6.2 Hz, 4H), 1.42 (m, 4H), 1.38-1.30 (m, 34H), 0.92 (t, J=6.8 Hz, 6H); $^{13}C$ NMR (100 MHz, $CDCl_3$ salient peaks corresponding to the cis (meso) derivative in large excess) δ (ppm) 87.4, 78.1, 69.1, 33.0, 31.2, 30.9, 29.8, 28.7, 26.2, 25.4, 24.9, 24.1, 23.3, 22.1, 13.3.

Example 3: Synthesis of (2R,5S)-2,5-bis((octadecyloxy)methyl)tetrahydrofuran and (2S,5S)-2,5-bis((octadecyloxy)methyl)tetrahydrofuran, B

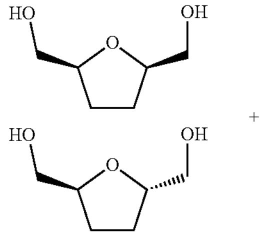

A

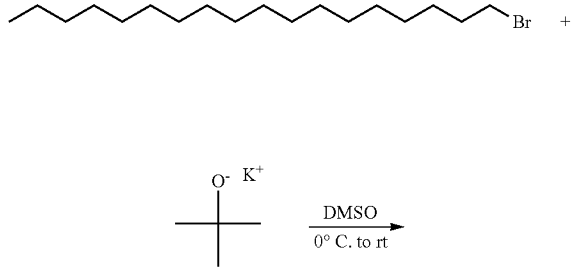

-continued

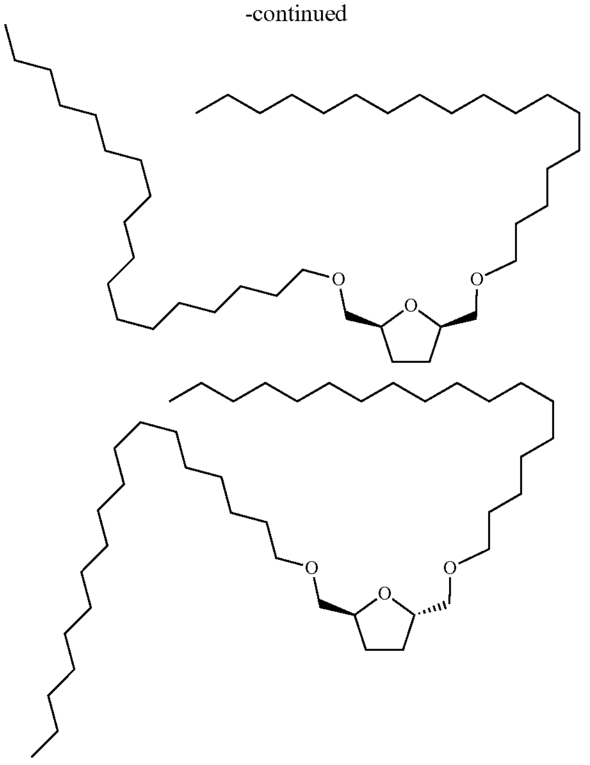

B

Experimental:

An oven dried, single neck 10 mL round bottomed flask equipped with a PTFE coated magnetic stir bar was charged with 50 mg of a 9:1 mixture of ((2R,5S)-tetrahydrofuran-2,5-diyl)dimethanol and ((2S,5S)-tetrahydrofuran-2,5-diyl)dimethanol (0.378 mmol) and 5 mL of anhydrous DMSO. The flask was then immersed in an ice-brine bath (~−10° C.) and, while stirring, 106 mg of potassium t-butoxide (0.946 mmol) added in portions and the mixture stirred for 30 minutes at this temperature. At this time, the neck was stoppered with a rubber septum and an argon gas inlet affixed via a 14" needle. While vigorously stirring and under an argon blanket, 277 μL of 1-bromooctadecane (0.832 mmol) was added via syringe. The mixture was then warmed to room temperature and continued to react overnight. After this time, an aliquot was removed and spotted on a silica gel TLC plate, which exhibited a single band (cerium molybdate stain) after developing in 11:1 hexanes/ethyl acetate. The signature band for A (baseline) was noticeably absent, suggesting this reagent had fully converted. Here, the mixture was diluted with 5 mL of water and 5 mL of methylene chloride and partitioned and the aqueous layer extracted with 3-5 mL volumes of methylene chloride. The organic phases were combined, dried with anhydrous magnesium sulfate, filtered and concentrated under vacuum. The oily residue was dissolved in a minimum amount of methylene chloride and added to 20 g of silica gel, which was then dried under vacuum, furnishing product adsorbed silica gel. This material was added to a pre-fabricated silica gel column, where flash chromatography with hexanes to 5% ethyl acetate in hexanes afforded 132 mg of a B as an off-white solid after concentration (55% of theoretical). $^{1}H$ NMR (400 MHz, $CDCl_3$, salient peaks corresponding to the cis (meso) derivative in large excess) δ (ppm) 4.20 (m, 2H), 3.63 (m, 2H), 3.41-3.38 (m, 4H), 2.08 (m, 2H), 1.65 (m, 2H), 1.48 (t, J=6.2 Hz, 4H), 1.41 (m, 4H), 1.40-1.28 (m, 58H), 0.89 (t, J=6.8 Hz, 6H); $^{13}C$ NMR (100 MHz, $CDCl_3$ salient peaks corresponding to the cis (meso) derivative in large excess) δ (ppm) 87.4, 78.1, 69.1, 33.0, 31.2, 30.9, 29.8, 28.7, 26.2, 25.4, 24.9, 24.1, 23.8, 23.3, 22.9, 22.7, 22.5, 22.1, 21.7, 21.3, 13.3.

B. bHMTHF Monoethers

Example 4: Synthesis of ((2S,5R)-5-((hexyloxy)methyl)tetrahydrofuran-2-yl)methanol, ((2S,5S)-5-((hexyloxy)methyl)tetrahydrofuran-2-yl)methanol, and ((2S,5S)-5-((hexyloxy)methyl)tetrahydrofuran-2-yl)methanol, B

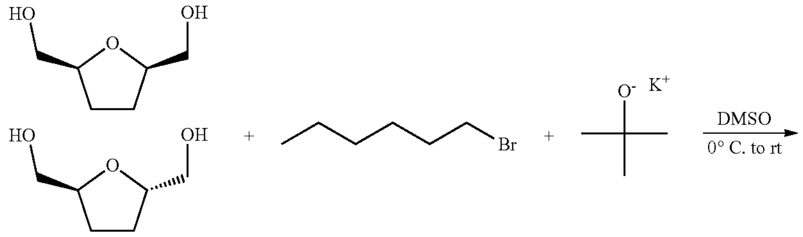

A

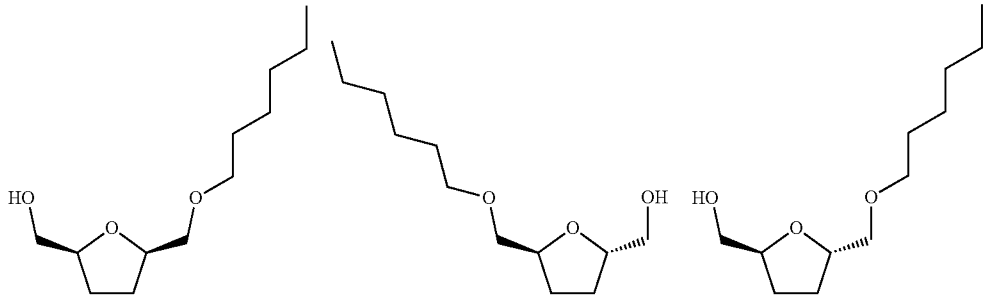

B

Experimental:

An oven dried, single neck 10 mL round bottomed flask equipped with a PTFE coated magnetic stir bar was charged with 50 mg of a 9:1 mixture of ((2R,5S)-tetrahydrofuran-2,5-diyl)dimethanol and ((2S,5S)-tetrahydrofuran-2,5-diyl)dimethanol (0.378 mmol) and 5 mL of anhydrous DMSO. The flask was then immersed in an ice-brine bath (~−10° C.) and, while stirring, 42 mg of potassium t-butoxide (0.378 mmol) added in portions and the mixture stirred for 30 minutes at this temperature. At this time, the neck was stoppered with a rubber septum and an argon gas inlet affixed via a 14" needle. While vigorously stirring and under an argon blanket, 53 μL of 1-bromohexane (0.378 mmol) was added via syringe. The mixture was then warmed to room temperature and continued to react overnight. After this time, an aliquot was removed and spotted on a silica gel TLC plate, which exhibited two salient bands (cerium molybdate stain) after developing in 3:1 hexanes/ethyl acetate, $Rf_1$=0.54 (targets B), $Rf_2$=baseline (unreacted THF-diols A). Analysis by GC/MS (EI, Initial 70° C., ramp 5° C. per minute to 350° C., hold for 60 min.) manifested three salient signals with retention times as follows: a) 12.4 min., m/z 132.1 (M+, unreacted THF-diols), b) 18.7 min., m/z 216.1 (M+, one or more of target monoethers), 19.2 min. m/z 216.1 (M+, one of more of the target mono-ethers).

Example 5: Synthesis of ((2S,5R)-5-((dodecyloxy)methyl)tetrahydrofuran-2-yl)methanol, ((2S,5S)-5-((dodecyloxy)methyl)tetrahydrofuran-2-yl)methanol, ((2S,5S)-5-((dodecyloxy)methyl)tetrahydrofuran-2-yl)methanol, B

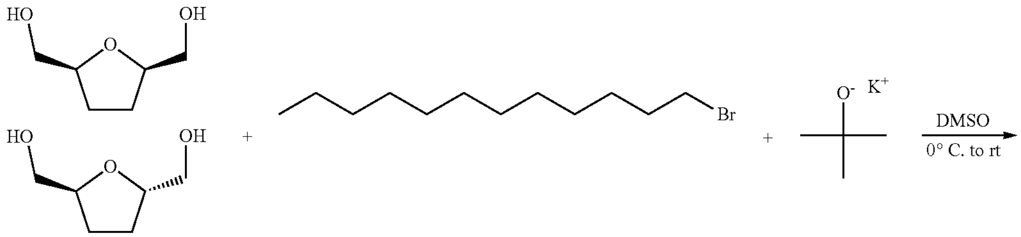

A

-continued

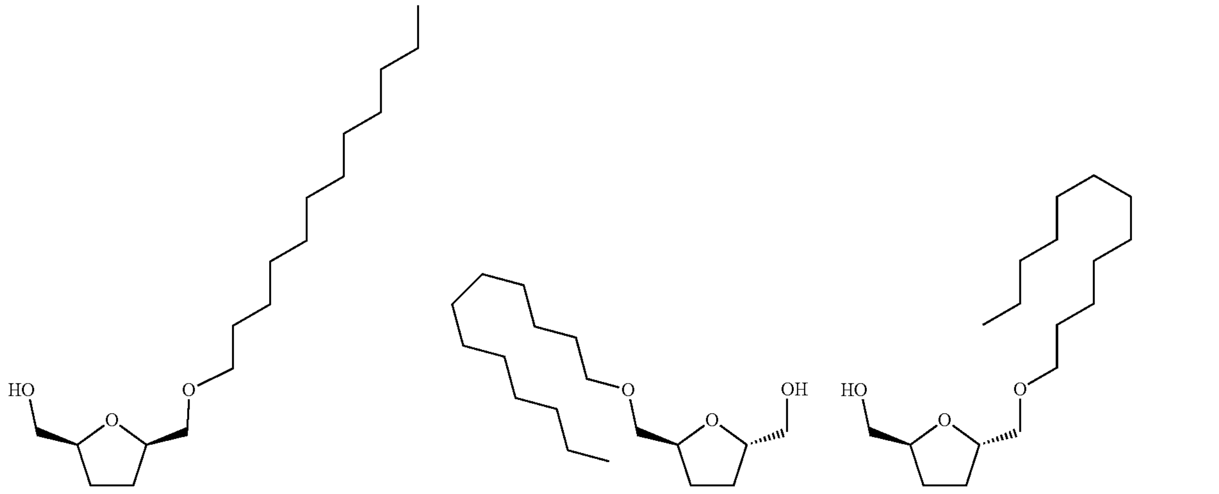

B

Experimental:

An oven dried, single neck 10 mL round bottomed flask equipped with a PTFE coated magnetic stir bar was charged with 50 mg of a 9:1 mixture of ((2R,5S)-tetrahydrofuran-2,5-diyl)dimethanol and ((2S,5S)-tetrahydrofuran-2,5-diyl)dimethanol (0.378 mmol) and 5 mL of anhydrous DMSO. The flask was then immersed in an ice-brine bath (~−10° C.) and, while stirring, 42 mg of potassium t-butoxide (0.378 mmol) added in portions and the mixture stirred for 30 minutes at this temperature. At this time, the neck was stoppered with a rubber septum and an argon gas inlet affixed via a 14" needle. While vigorously stirring and under an argon blanket, 91 μL of 1-bromododecane (0.378 mmol) was added via syringe. The mixture was then warmed to room temperature and continued to react overnight. After this time, an aliquot was removed and spotted on a silica gel TLC plate, which exhibited two salient bands (cerium molybdate stain) after developing in 5:1 hexanes/ethyl acetate, $Rf_1$=0.57 (targets B), $Rf_2$=baseline (residual THF-diols A). Analysis by GC/MS (EI, Initial 70° C., ramp 5° C. per minute to 350° C., hold for 60 min.) manifested three salient signals with retention times as follows: a) 12.3 min., m/z 132.1 (M+, unreacted THF-diols A), b) 25.1 min., m/z 300.2 (M+, one or more of target monoethers), 25.9 min. m/z 300.2 (M+, one of more of the target mono-ethers).

Example 6: Synthesis of ((2S,5R)-5-((octadecyloxy)methyl)tetrahydrofuran-2-yl)methanol, ((2S,5S)-5-((octadecyloxy)methyl)tetrahydrofuran-2-yl)methanol, ((2S,5S)-5((octadecyloxy)methyl)tetrahydrofuran-2-yl)methanol, B

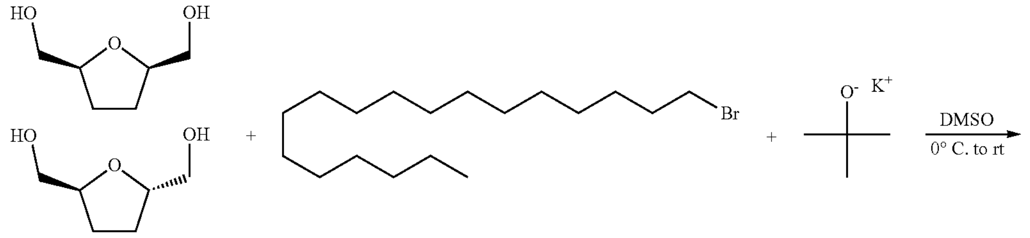

A

-continued

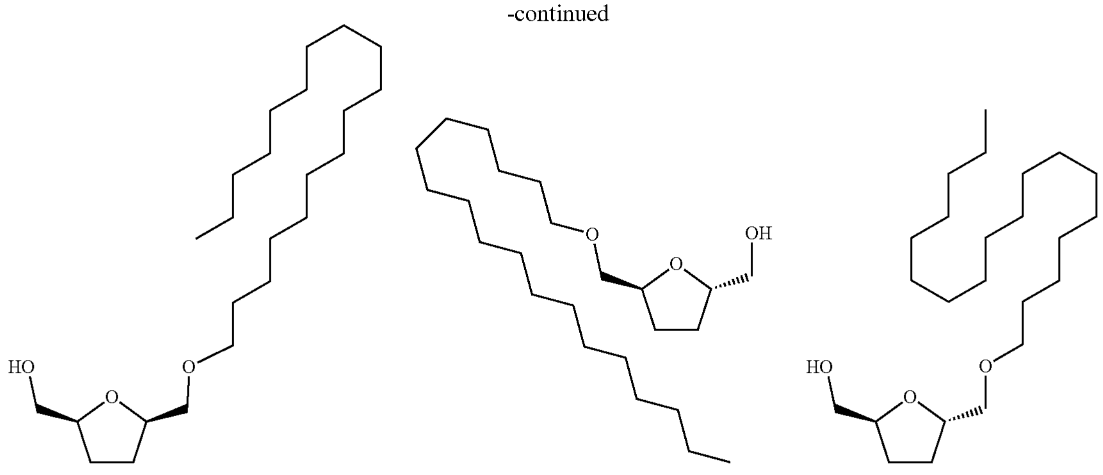

B

Experimental:

An oven dried, single neck 10 mL round bottomed flask equipped with a PTFE coated magnetic stir bar was charged with 50 mg of a 9:1 mixture of ((2R,5S)-tetrahydrofuran-2,5-diyl)dimethanol and ((2S,5S)-tetrahydrofuran-2,5-diyl)dimethanol (0.378 mmol) and 5 mL of anhydrous DMSO. The flask was then immersed in an ice-brine bath (~−10° C.) and, while stirring, 42 mg of potassium t-butoxide (0.378 mmol) added in portions and the mixture stirred for 30 minutes at this temperature. At this time, the neck was stoppered with a rubber septum and an argon gas inlet affixed via a 14" needle. While vigorously stirring and under an argon blanket, 126 μL of 1-bromododecane (0.378 mmol) was added via syringe. The mixture was then warmed to room temperature and continued to react overnight. After this time, an aliquot was removed and spotted on a silica gel TLC plate, which exhibited a single band (cerium molybdate stain) after developing in 6:1 hexanes/ethyl acetate, $Rf_1$=0.62 (targets B) and $Rf_2$=baseline (unreacted THF-diols A). The signature band for A was patently absent, suggesting this reagent had fully converted. Analysis by LC/MS (APCI-, RP 1.7 μm, 2.1×50 mm, mobile phase-gradient 50 to 0% aqueous in $CH_3CN$, flow rate 0.5 mL/min., M−1) m/z 383.4.

C. Derivatives of bHMTHF Monoethers

Example 7: Synthesis of potassium ((2S,5R)-5-((hexyloxy)methyl)tetrahydrofuran-2-yl)methyl sulfate and diastereomers, B

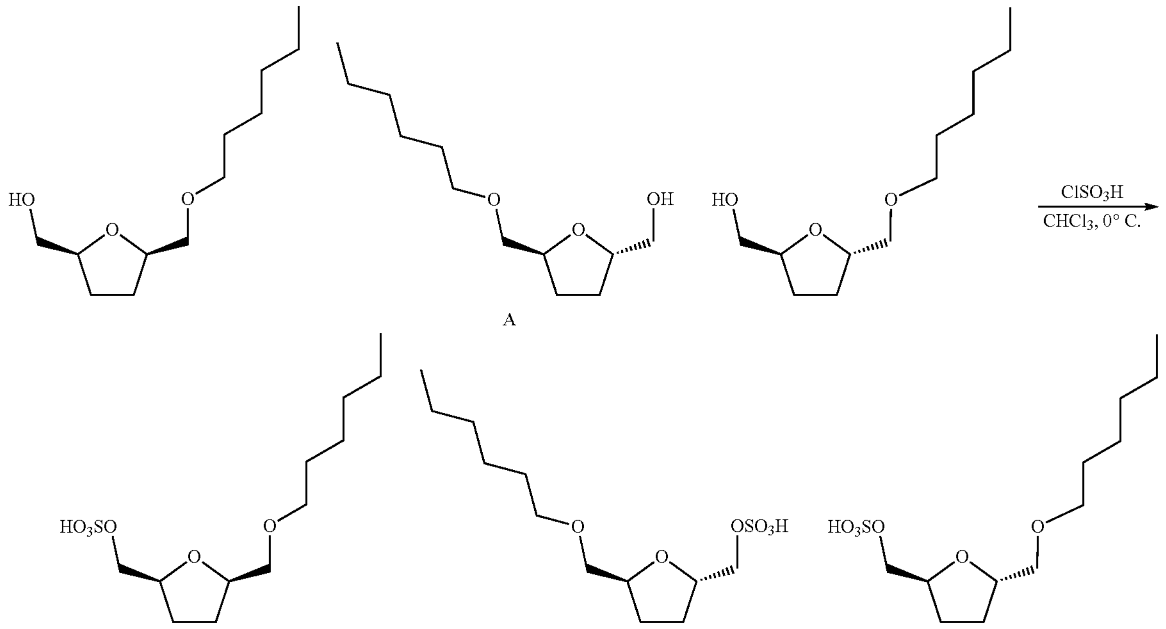

A

B

Experimental:

An oven dried, single neck 10 mL round bottomed flask equipped with a 0.5" PTFE coated tapered magnetic stir bar was charged with 50 mg of a 9:1 mixture of ((2S,5R)-5-((hexyloxy)methyl)tetrahydrofuran-2-yl)methanol and diastereomers A (0.231 mmol) and 5 mL of anhydrous $CHCl_3$. The flask was then immersed in an ice-brine bath (~−10° C.) and, while stirring, 15.4 μL of chlorosulfonic acid (26.9 mg, 0.231 mmol) was added dropwise over 15 minutes. The mixture was then warmed to room temperature and continued to react for 1 hour. After this time, the solvent and resultant HCl was removed via rotary evaporation and high vacuum. The light yellow oily residue dissolved in a minimum amount of isopropanol and placed in a freezer. After about 3 days, suspended crystals were observed, which were filtered and dried, affording 16 mg (24% of theoretical) of B. Elemental analysis (C, H): Predicted for $C_{12}H_{24}O_6S$ (C, 48.63; H, 8.16). Found (C, 48.66; H, 8.23).

Example 8: Synthesis of 2-(2-((((2S,5R)-5-((dodecyloxy)methyl)tetrahydrofuran2yl)methyl)amino)-ethoxy)ethanol and diastereomers C (plausible non-ionic surfactant)

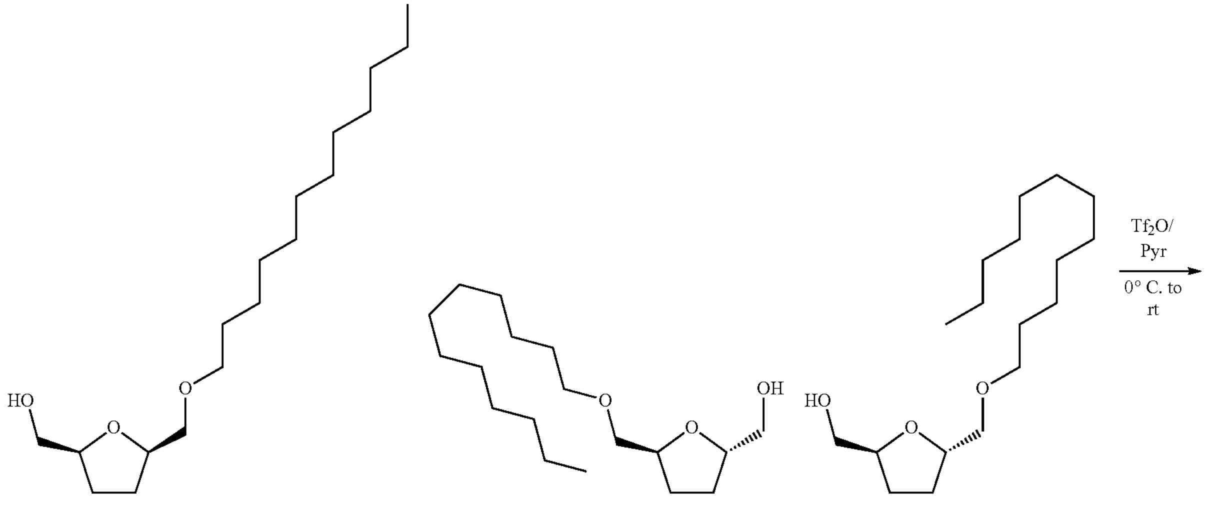

A

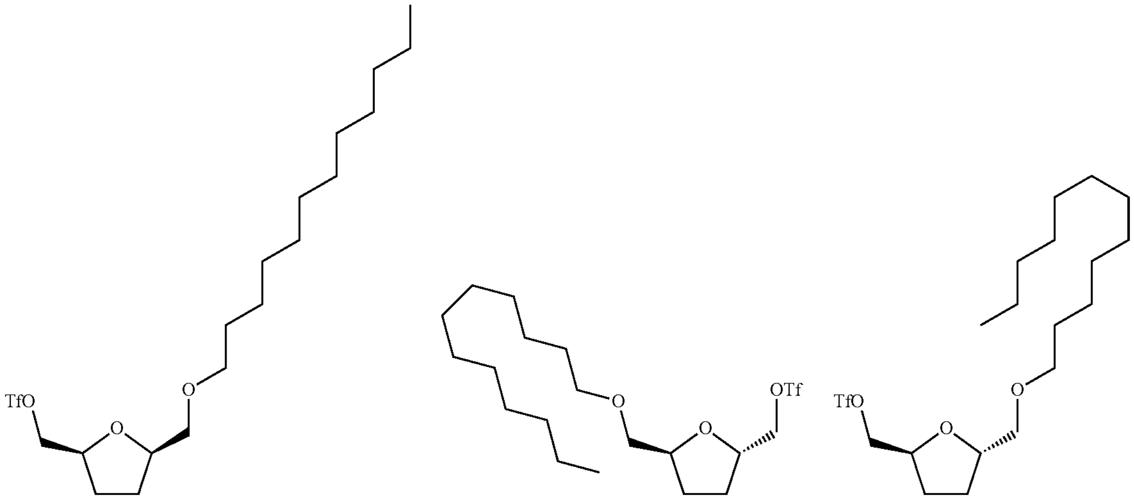

B

-continued

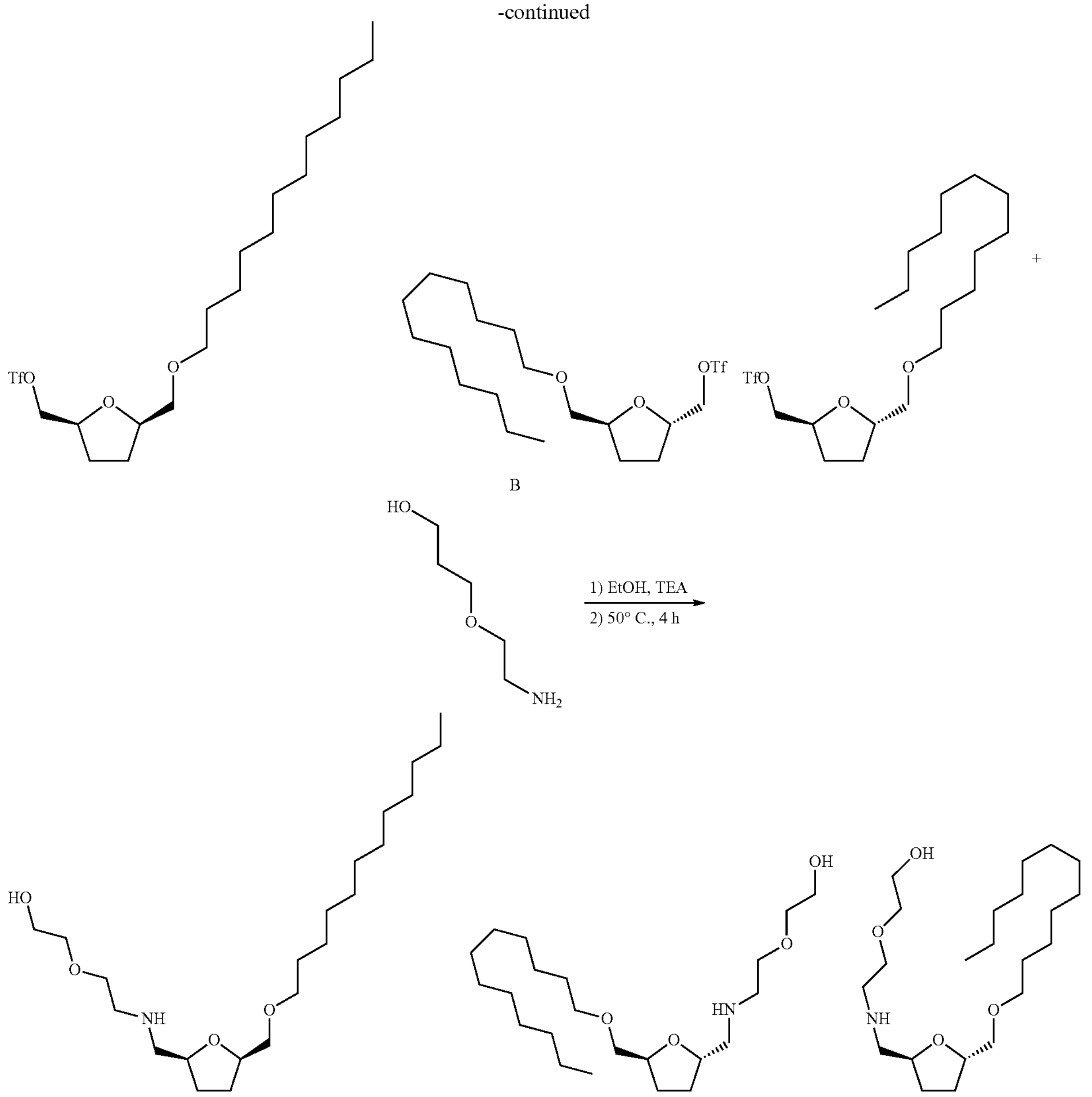

B

C

Experimental:

An oven dried, single neck 25 mL round bottomed flask equipped with a 0.5" PTFE coated octagonal magnetic stir bar was charged with 200 mg of a 9:1 mixture of ((2S,5R)-5-((dodecyloxy)methyl)tetrahydrofuran-2-yl)methanol and diastereomers A (0.666 mmol), 107 μL of pyridine (1.33 mmol) and 5 mL of anhydrous methylene chloride. The flask was then immersed in an ice-brine bath (~−10° C.) and, while stirring, 112 μL of triflic anhydride (0.666 mmol) was added dropwise over 15 minutes. The mixture was then warmed to room temperature and continued to react for 2 hour. After this time, an aliquot was removed and spotted on a silica gel TLC plate that was developed using a 25% ethyl acetate eluent. One spot appeared on the plate (cerium molybdate visualization) with an Rf=0.57. The absence of the band corresponding to the starting alcohol, Rf=0.44, signified complete conversion. Excess solvent was then evaporated, furnishing 261 mg of a light yellow oil (90%) specifying B. This material was used in the subsequent step without further purification.

A single neck 50 mL round bottomed flask equipped with a 5/8" octagonal PTFE coated magnetic stir bar and was charged with 250 mg of B (0.578 mmol), 69 mg of 3-(2-aminoethoxy)propan-1-ol, 81 μL of triethylamine (0.578 mmol) and 10 mL of absolute ethanol. A reflux condenser was outfitted to the flask, and while stirring, the solution was heated to 50° C., 4 hours. After this time, an aliquot was extracted and analyzed by TLC (cerium molybdate visualization), demonstrating that B had entirely disappeared. The mixture was poured directly onto a short-path, pre-fabricated column comprised of neutral alumina, where flash chromatography with absolute ethanol afforded 96 mg of C as a viscous, pale yellow oil (43%). $^{1}$H NMR (400 MHz, $CDCl_3$, salient peaks corresponding to the cis (meso) species) δ (ppm) 4.12 (m, 1H), 4.03 (m, 1H), 3.64-3.62 (m, 4H), 3.53 (t, J=5.4 Hz, 2H), 3.41 (t, J=6.0 Hz, 2H), 3.30 (t, J=5.4 Hz), 2.75-2.72 (m, 3H), 2.59 (m, 1H), 2.01 (m, 2H), 1.71 (m, 2H), 1.47 (t, J=5.6 Hz, 2H), 1.38 (m, 2H), 1.33-1.27 (m, 16H), 0.93 (t, J=6.8 Hz, 3H); $^{13}C$ NMR (100 MHz, $CDCl_3$, salient peaks (cis, meso)) δ (ppm) 84.1, 82.2, 77.8, 73.6, 69.0, 68.4, 63.2, 55.9, 50.0, 32.4, 31.9, 31.4, 30.8, 30.6, 30.5, 30.2, 29.9, 29.7, 29.6, 29.3, 29.1, 16.0.
Example 9: Synthesis of ((2S,5R)-5-((octadecyloxy)methyl)tetrahydrofuran-2-yl)methanaminium chloride and diastereomers D (plausible cationic surfactants)
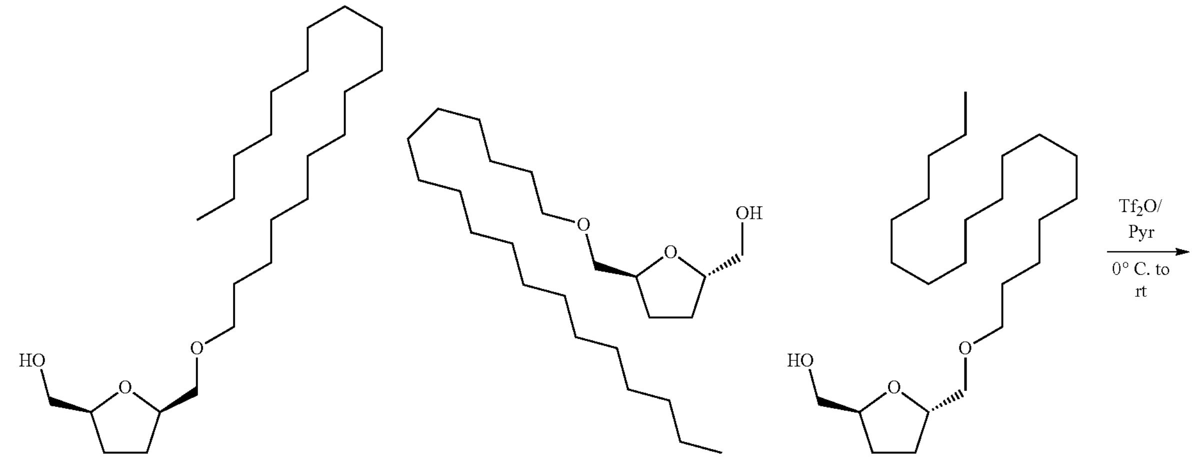
A
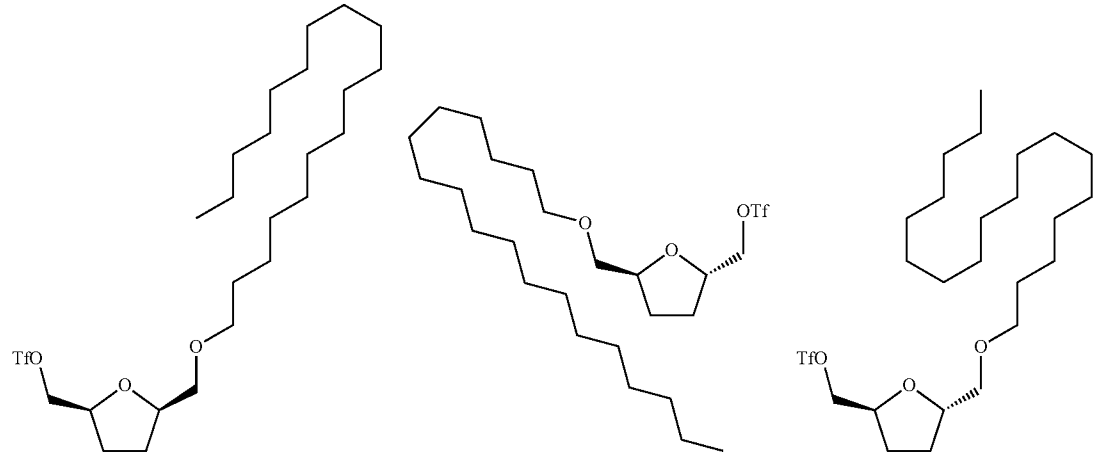
B
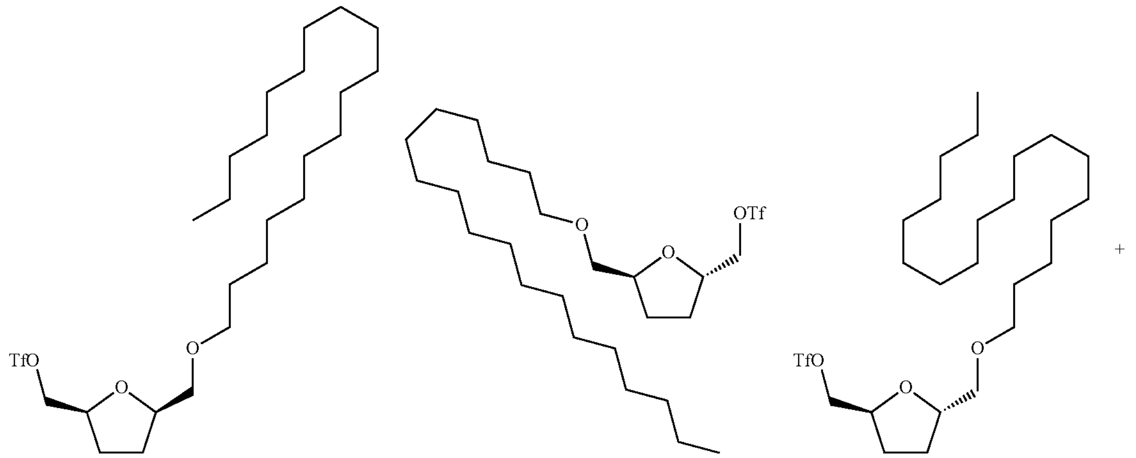
B -continued

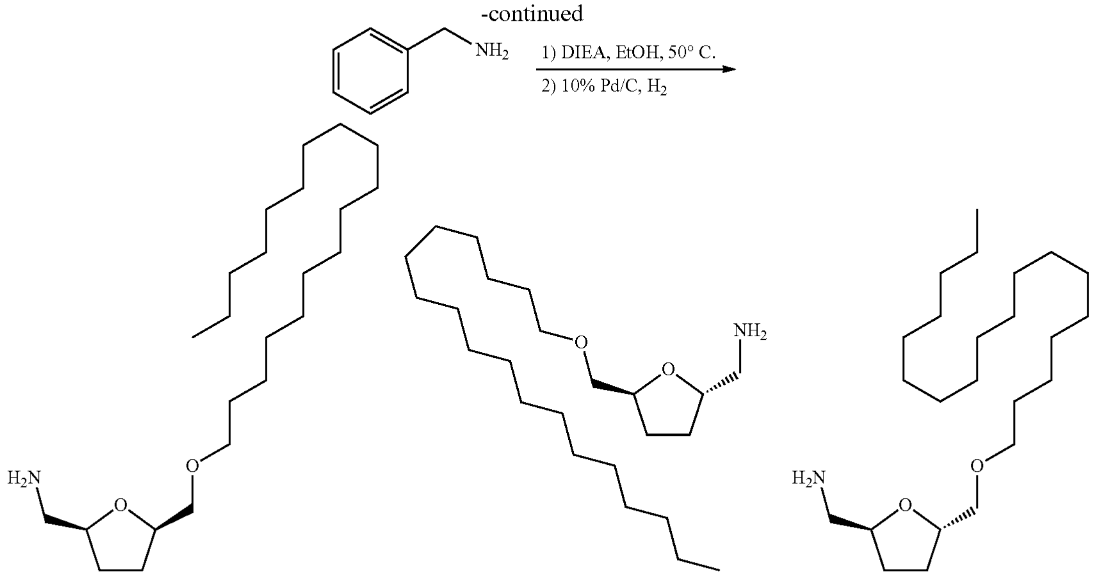

C

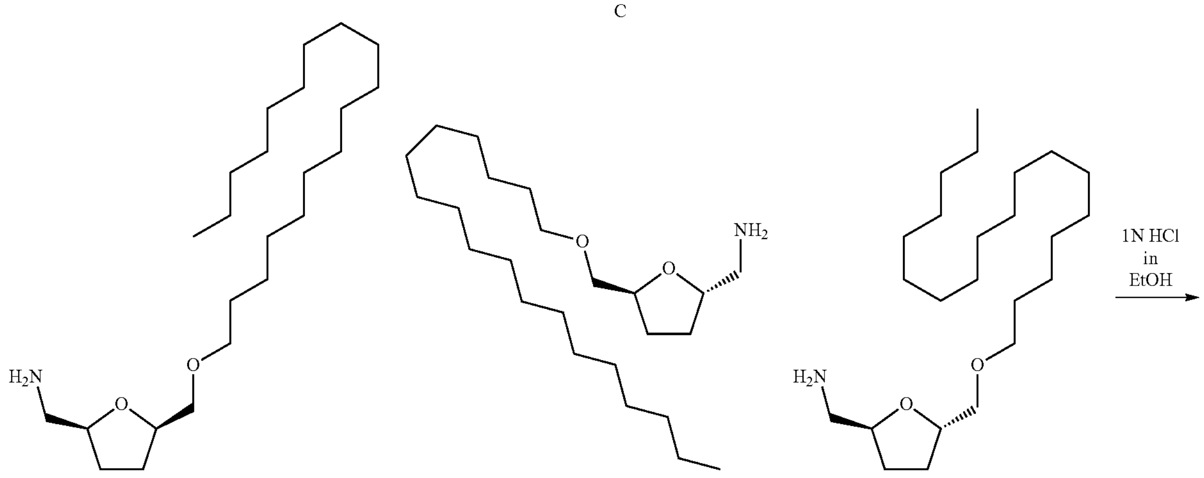

C

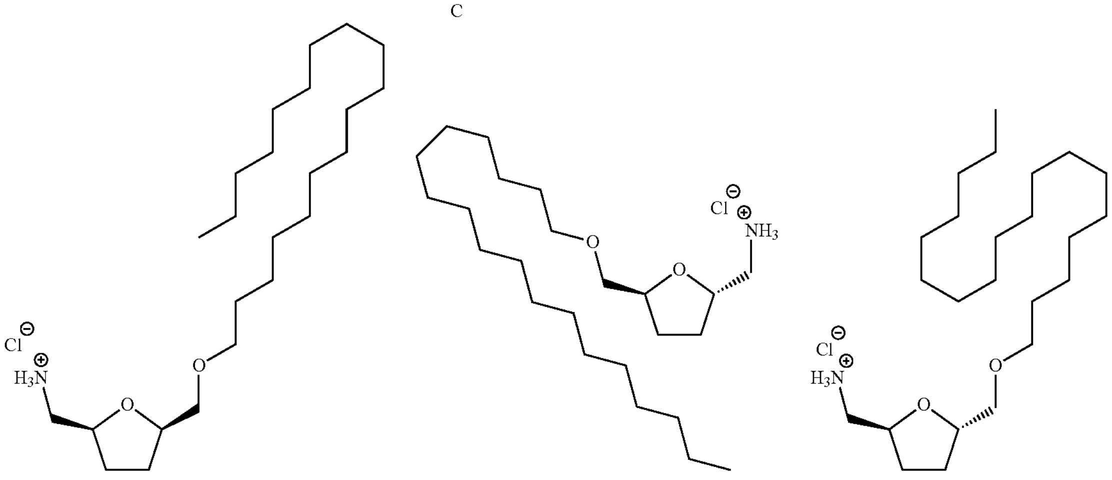

D

Experimental:

An oven dried, 25 mL single neck round bottomed flask equipped with a tapered 1 cm PTFE coated magnetic stir bar was charged with 150 mg of A (0.390 mmol), 94 μL of pyridine (1.17 mmol) and 10 mL of anhydrous methylene chloride. The flask was then immersed in brine/ice bath (~−10° C.), and while vigorously stirring, 66 μL of triflic anhydride (0.390 mmol) was added dropwise over 10 minutes. The ice bath was then removed and reaction continued at room temperature for 2 h. After this time, an aliquot was removed, spotted on a silica gel TLC plate and developed with 20% ethyl acetate in hexanes, indicating (cerium molybdate visualization) a single band with an Rf=0.52. The signature band for A, Rf=0.39, was patently absent, indicating this reagent had fully converted. Solids were then filtered and filtrate concentrated in vacuo overnight, furnishing 173 mg of B as a light brown oil (88%). This product was used in the next step without further purification.

A single neck, 50 mL round bottomed flask equipped with a 1 cm PTFE coated magnetic stir bar was charged with 175 mg of B (0.339 mmol), 65 μL of Hunig's base (0.373 mmol), 37 μL of benzylamine and 10 mL of ethanol. The neck was capped with a reflux condenser, and while vigorously stirring, the mixture was heated to 50° C. for 2 hrs. After this time, TLC (UV and cerium molybdate visualization) indicated a single band and full consumption of both reagents. The mixture was then diluted with 10 mL of water and 10 mL of methylene chloride and layers partitioned by liquid-liquid extraction. The aqueous layer was extracted with 5 mL volumes of methylene chloride (×2), organic layers combined and dried, affording a pale yellow waxy solid. This material was charged to a 25 mL round bottomed flask equipped with a 0.5" PTFE coated magnetic stir bar, along with 100 mg of 10% Pd/C and 10 mL of absolute ethanol. The neck was capped with a rubber septum and a balloon filled with $H_2$ was inserted via a 9 inch, 16" needle; the mixture was stirred vigorously and monitored by TLC (UV-vis visualization). After 2 h, the reaction was deemed complete; catalyst filtered through a pad of Celite and filtrate concentrated under vacuum overnight, affording 74 mg of C (52%) as light yellow, loose oil. This material was used in the supervening step without further purification.

A single neck, 10 mL round bottomed flask equipped with a 0.5" octagonal PTFE coated magnetic stir bar was charged with 50 mg of C (0.130 mmol) and 2 mL of a 1N ethanolic HCl solution. The mixture was stirred for 15 minutes, after which time excess solvent was removed first with a rotary evaporator (50° C., 30 mmHg) then under high vacuum (<1 torr) for 1 week. After this time, a yellow semi-solid corresponding to D was observed, weighing 49 mg (88%). $^1H$ NMR (400 MHz, $d^6$-DMSO/$D_2O$, salient signals corresponding to the cis (meso) derivative) δ (ppm) 4.52 (m, 1H), 4.13 (m, 1H), 3.62-3.60 (m, 2H), 3.32-3.28 (m, 4H), 2.03 (m, 2H), 1.75 (m, 2H), 1.59 (m, 2H), 1.48 (m, 2H), 1.30-1.25 (m, 28H), 0.95 (t, J=6.2 Hz, 3H). 13C NMR (100 MHz, $d^6$-DMSO/$D_2O$ salient signals corresponding to the cis (meso) derivative) δ (ppm) 85.1, 81.2, 77.3, 72.2, 49.2, 32.6, 32.2, 31.9, 31.5, 31.2, 30.5, 30.3, 30.0, 29.8, 29.6, 29.3, 29.1, 28.9, 28.8, 28.6, 28.3, 28.0, 27.9, 13.1.

D. FDM Diethers

Example 10: Synthesis of 2,5-bis((hexyloxy)methyl)furan, B

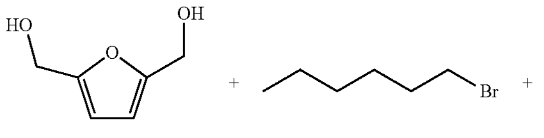

A

-continued

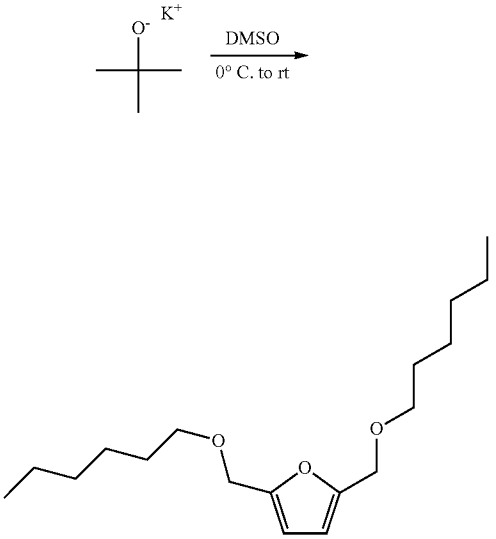

B

Experimental:

An oven dried, single neck 10 mL round bottomed flask equipped with a PTFE coated magnetic stir bar was charged with 100 mg of FDM A (0.780 mmol) and 5 mL of anhydrous DMSO. The flask was then immersed in an ice-brine bath (~−10° C.) and, while stirring, 219 mg of potassium t-butoxide (1.95 mmol) added in portions and the mixture stirred for 30 minutes at this temperature. At this time, the neck was stoppered with a rubber septum and an argon gas inlet affixed via a 14" needle. While vigorously stirring and under an argon blanket, 240 μL of 1-bromohexane (1.72 mmol) was added via syringe. The mixture was then warmed to room temperature and continued to react overnight. After this time, an aliquot was removed and spotted on a silica gel TLC plate, which exhibited a single band (cerium molybdate stain) after developing in 9:1 hexanes/ethyl acetate. The signature band for FDM A (baseline) was patently absent, suggesting this reagent had fully converted. Here, the mixture was diluted with 5 mL of water and 5 mL of methylene chloride and partitioned and the aqueous layer extracted with 3-5 mL volumes of methylene chloride. The organic phases were combined, dried with anhydrous magnesium sulfate, filtered and concentrated under vacuum. The oily residue was dissolved in a minimum amount of methylene chloride and added to 20 g of silica gel, which was then dried under vacuum, furnishing product adsorbed silica gel. This material was added to a pre-fabricated silica gel column, where flash chromatography with hexanes to 13% ethyl acetate in hexanes afforded 124 mg of a B as light yellow oil after concentration in vacuo (53% of theoretical). $^1H$ NMR (400 MHz, $CDCl_3$) δ (ppm) 6.32 (s, 2H), 4.63 (s, 4H), 3.40-3.36 (m, 4H), 2.10 (m, 2H), 1.59 (m, 2H), 1.48 (t, J=6.0 Hz, 4H), 1.42 (m, 4H), 1.35-1.30 (m, 10H), 0.91 (t, J=7.4 Hz, 6H); $^{13}C$ NMR (100 MHz, $CDCl_3$) δ (ppm) 152.23, 108.3, 71.6, 68.1, 32.6, 31.4, 29.8, 25.4, 13.3.

Example 11: Synthesis of 2,5-bis((dodecyloxy)methyl)furan, B

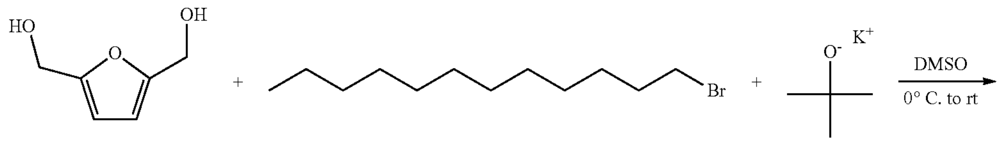

A

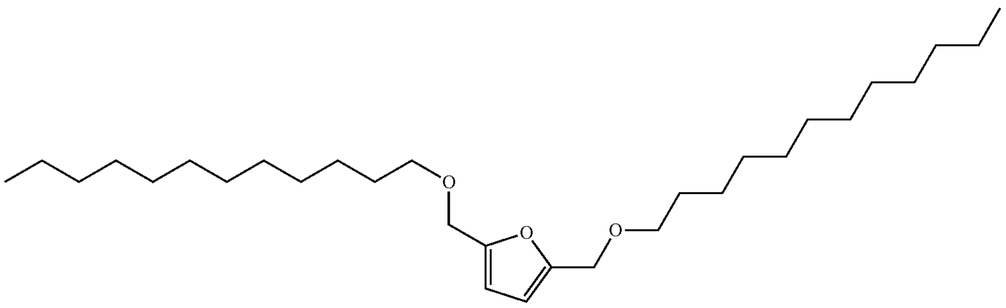

B

Experimental:

An oven dried, single neck 10 mL round bottomed flask equipped with a PTFE coated magnetic stir bar was charged with 100 mg of FDM A (0.780 mmol) and 5 mL of anhydrous DMSO. The flask was then immersed in an ice-brine bath (~−10° C.) and, while stirring, 219 mg of potassium t-butoxide (1.95 mmol) added in portions and the mixture stirred for 30 minutes at this temperature. At this time, the neck was stoppered with a rubber septum and an argon gas inlet affixed via a 14" needle. While vigorously stirring and under an argon blanket, 412 μL of 1-bromododecane (1.72 mmol) was added via syringe. The mixture was then warmed to room temperature and continued to react overnight. After this time, an aliquot was removed and spotted on a silica gel TLC plate, which exhibited a single band (cerium molybdate stain) after developing in 10:1 hexanes/ethyl acetate. The signature band for FDM A (baseline) was noticeably absent, suggesting this reagent had fully converted. Here, the mixture was diluted with 5 mL of water and 5 mL of methylene chloride and partitioned and the aqueous layer extracted with 3-5 mL volumes of methylene chloride. The organic phases were combined, dried with anhydrous magnesium sulfate, filtered and concentrated under vacuum. The oily residue was dissolved in a minimum amount of methylene chloride and added to 20 g of silica gel, which was then dried under vacuum, furnishing product adsorbed silica gel. This material was added to a prefabricated silica gel column, where flash chromatography with hexanes to 9% ethyl acetate in hexanes afforded 139 mg of a B as a beige solid after concentration (39% of theoretical). $^{1}H$ NMR (400 MHz, $CDCl_3$) δ (ppm) 6.42 (2, 2H), 4.67 (s, 4H), 3.42-3.39 (m, 4H), 2.06 (m, 2H), 1.58 (m, 2H), 1.47 (t, J=6.4 Hz, 4H), 1.40 (m, 4H), 1.38-1.30 (m, 34H), 0.91 (t, J=7.0 Hz, 6H); $^{13}C$ NMR (100 MHz, $CDCl_3$) δ (ppm) 152.4, 108.5, 73.4, 69.9, 33.0, 31.2, 30.9, 29.8, 28.7, 26.2, 25.4, 24.9, 24.1, 23.3, 22.1, 13.3.

Example 12: Synthesis of 2,5-bis((octadecyloxy)methyl)furan, B

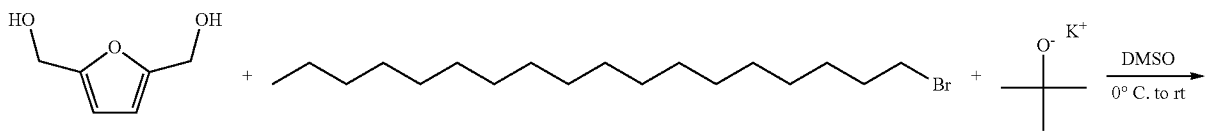

A

-continued

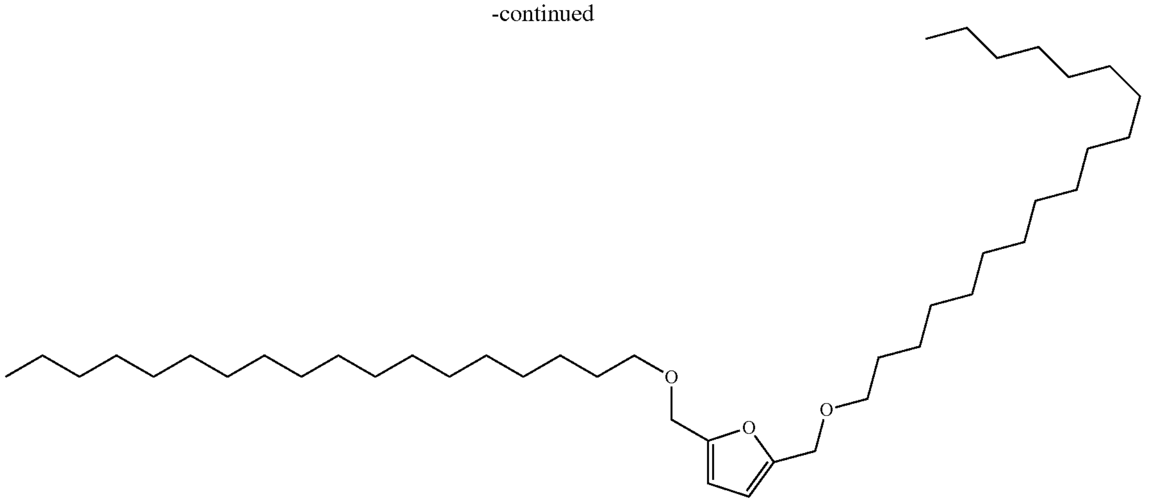

B

Experimental:

An oven dried, single neck 10 mL round bottomed flask equipped with a PTFE coated magnetic stir bar was charged with 100 mg of FDM A (0.780 mmol) and 5 mL of anhydrous DMSO. The flask was then immersed in an ice-brine bath (~−10° C.) and, while stirring, 219 mg of potassium t-butoxide (1.95 mmol) added in portions and the mixture stirred for 30 minutes at this temperature. At this time, the neck was stoppered with a rubber septum and an argon gas inlet affixed via a 14" needle. While vigorously stirring and under an argon blanket, 586 μL of 1-bromooctadecane (1.72 mmol) was added via syringe. The mixture was then warmed to room temperature and continued to react overnight. After this time, an aliquot was removed and spotted on a silica gel TLC plate, which exhibited a single band (cerium molybdate stain) after developing in 11:1 hexanes/ethyl acetate. The signature band for FDM A (baseline) was noticeably absent, suggesting this reagent had fully converted. Here, the mixture was diluted with 5 mL of water and 5 mL of methylene chloride and partitioned and the aqueous layer extracted with 3-5 mL volumes of methylene chloride. The organic phases were combined, dried with anhydrous magnesium sulfate, filtered and concentrated under vacuum. The oily residue was dissolved in a minimum amount of methylene chloride and added to 20 g of silica gel, which was then dried under vacuum, furnishing product adsorbed silica gel. This material was added to a prefabricated silica gel column, where flash chromatography with hexanes to 6% ethyl acetate in hexanes afforded 171 mg of a B as an off-white solid after concentration (35% of theoretical). $^{1}H$ NMR (400 MHz, $CDCl_3$), δ (ppm) 6.40 (s, 2H), 4.52 (s, 4H), 3.41-3.38 (m, 4H), 2.08 (m, 2H), 1.65 (m, 2H), 1.48 (t, J=6.2 Hz, 4H), 1.41 (m, 4H), 1.40-1.28 (m, 58H), 0.89 (t, J=6.8 Hz, 6H); $^{13}C$ NMR (100 MHz, $CDCl_3$) δ (ppm) 152.7, 108.6, 73.6, 69.0, 33.0, 31.2, 30.9, 29.8, 28.7, 26.2, 25.4, 24.9, 24.1, 23.8, 23.3, 22.9, 22.5, 22.1, 21.7, 21.3, 13.3.

E. FDM Mono-Ethers

Example 13: Synthesis of (5-((octadecyloxy)methyl)furan-2-yl)methanol, B

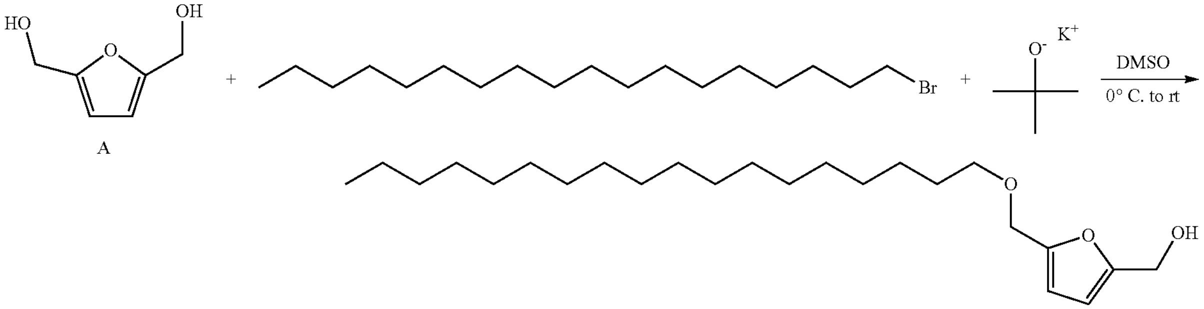

B

Experimental:

An oven dried, single neck 10 mL round bottomed flask equipped with a PTFE coated magnetic stir bar was charged with 100 mg FDM A (0.780 mmol) and 5 mL of anhydrous DMSO. The flask was then immersed in an ice-brine bath (~−10° C.) and, while stirring, 87 mg of potassium t-butoxide (0.780 mmol) added in portions and the mixture stirred for 30 minutes at this temperature. At this time, the neck was stoppered with a rubber septum and an argon gas inlet affixed via a 14" needle. While vigorously stirring and under an argon blanket, 266 μL of 1-bromooctadecane (0.780 mmol) was added via syringe. The mixture was then warmed to room temperature and continued to react overnight. After this time, an aliquot was removed and spotted on a silica gel TLC plate, which exhibited three bands (cerium molybdate stain) after developing in 6:1 hexanes/ethyl acetate, $Rf_1$=0.91 (FDM di-ether) and $Rf_2$=0.60, and baseline (unreacted FDM A). The signature band for A was patently absent, suggesting this reagent had fully converted. Analysis by LC/MS (APCI-, RP 1.7 μm, 2.1×50 mm, mobile phase-gradient 50 to 0% aqueous in $CH_3CN$, flow rate 0.5 mL/min., M−1) divulged a m/z of 379.3.

Example 14: Synthesis of (5-((dodecyloxy)methyl)furan-2-yl)methanol, B

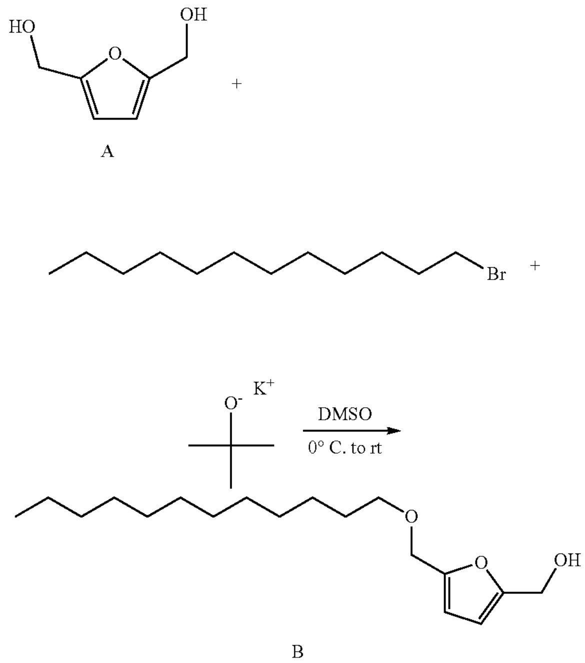

Experimental:

An oven dried, single neck 10 mL round bottomed flask equipped with a PTFE coated magnetic stir bar was charged with 100 mg FDM A (0.780 mmol) and 5 mL of anhydrous DMSO. The flask was then immersed in an ice-brine bath (~−10° C.) and, while stirring, 87 mg of potassium t-butoxide (0.780 mmol) added in portions and the mixture stirred for 30 minutes at this temperature. At this time, the neck was stoppered with a rubber septum and an argon gas inlet affixed via a 14" needle. While vigorously stirring and under an argon blanket, 187 μL of 1-bromododecane (0.780 mmol) was added via syringe. The mixture was then warmed to room temperature and continued to react overnight. After this time, an aliquot was removed and spotted on a silica gel TLC plate, which exhibited two salient bands (cerium molybdate stain) after developing in 5:1 hexanes/ethyl acetate, $Rf_1$=0.91 (FDM-diether), $Rf_2$=0.55 (targets B), $Rf_3$=baseline (FDM A). Analysis by GC/MS (EI, Initial 70° C., ramp 5° C. per minute to 350° C., hold for 60 min.) manifested three salient signals with retention times as follows: a) 11.3 min., m/z 128.1 (M+, FDM A), b) 24.2 min., m/z 296.2 (M+, FDM-monoether B).

Example 15: Synthesis of (5-((hexyloxy)methyl)furan-2-yl)methanol, B

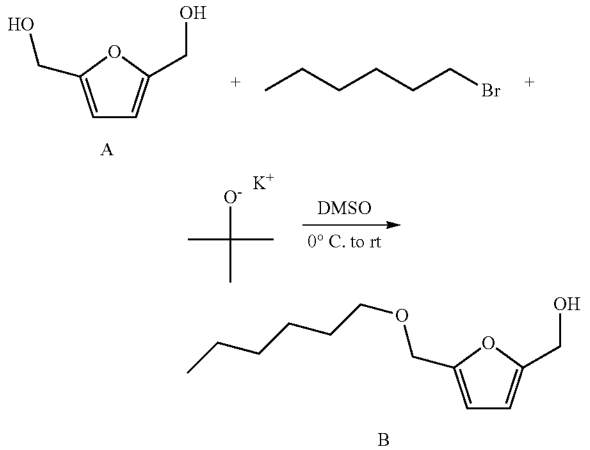

Experimental:

An oven dried, single neck 10 mL round bottomed flask equipped with a PTFE coated magnetic stir bar was charged with 100 mg FDM A (0.780 mmol) and 5 mL of anhydrous DMSO. The flask was then immersed in an ice-brine bath (~−10° C.) and, while stirring, 87 mg of potassium t-butoxide (0.780 mmol) added in portions and the mixture stirred for 30 minutes at this temperature. At this time, the neck was stoppered with a rubber septum and an argon gas inlet affixed via a 14" needle. While vigorously stirring and under an argon blanket, 109 μL of 1-bromohexane (0.780 mmol) was added via syringe. The mixture was then warmed to room temperature and continued to react overnight. After this time, an aliquot was removed and spotted on a silica gel TLC plate, which exhibited three bands (cerium molybdate stain) after developing in 3:1 hexanes/ethyl acetate, $Rf_1$=0.89 (FDM di-ether), $Rf_2$=0.57 (target B), $Rf_3$=baseline (unreacted FDM A). Analysis by GC/MS (EI, Initial 70° C., ramp 5° C. per minute to 350° C., hold for 60 min.) manifested three salient signals with retention times as follows: a) 11.3 min., m/z 128.1 (M+, unreacted THF-diols), b) 17.6 min., m/z 212.1 (M+, FDM mono-ether, B).

F. Amphiphilic Derivatives of FDM Mono-Ethers

Generally, various derivative species can also be made from FDM-monoethers, and the preparation of the FDM derivatives employ the same or similar reaction protocols, mutatis mutandis, as that used to synthesize the derivatives from bHMTHF as a starting material, such as described in the foregoing examples. Hence, as a person of ordinary skill will comprehend, rather than repeat the entire series of examples for synthesis of derivatives from FDM mono-ethers, the following examples are of alternative compounds that illustrate certain variance in synthesis. Each of the compounds in these variant examples is expected to parallel that of a derivative bHMTHF mono-ether (e.g., non-hydrolyzable amphiphiles with potential applications as surfactants, dispersants, plasticizers, etc).

Example 16: Synthesis of (5-((dodecyloxy)methyl)furan-2-yl)methyl hydrogen sulfate, B

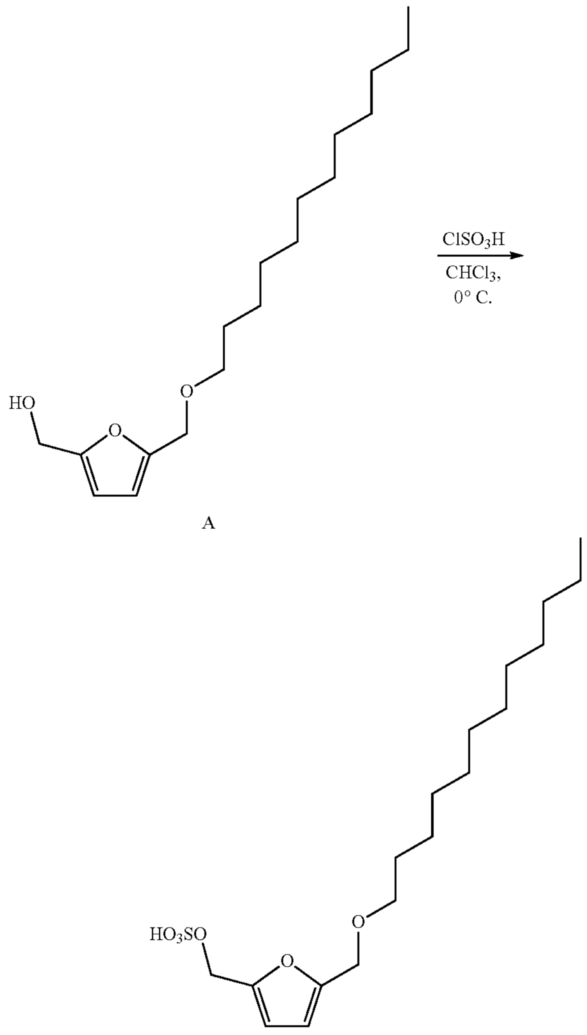

A

B

Experimental:

An oven dried, single neck 10 mL round bottomed flask equipped with a 0.5" PTFE coated tapered magnetic stir bar was charged with 100 mg of (5-((dodecyloxy)methyl)furan-2-yl)methanol A (0.337 mmol) and 5 mL of anhydrous $CHCl_3$. The flask was then immersed in an ice-brine bath (~−10° C.) and, while stirring, 22.5 μL of chlorosulfonic acid (39.2 mg, 0.231 mmol) was added dropwise over 15 minutes. The mixture was then warmed to room temperature and continued to react for 1 hour. After this time, the solvent and resultant HCl was removed via rotary evaporation and high vacuum. The light yellow oily residue dissolved in a minimum amount of isopropanol and placed in a freezer overnight. An abundance of suspended crystals were manifest that were filtered and dried, affording 55 mg (43% of theoretical) of B. Elemental analysis (C, H): Predicted for $C_{18}H_{32}O_6S$ (C, 57.42; H, 8.57). Found (C, 57.51; H, 8.60).

Example 17: Synthesis of 2-((2-(((5-((octadecyloxy)methyl)furan-2-yl)methyl)amino)ethyl)amino)-ethanol, C

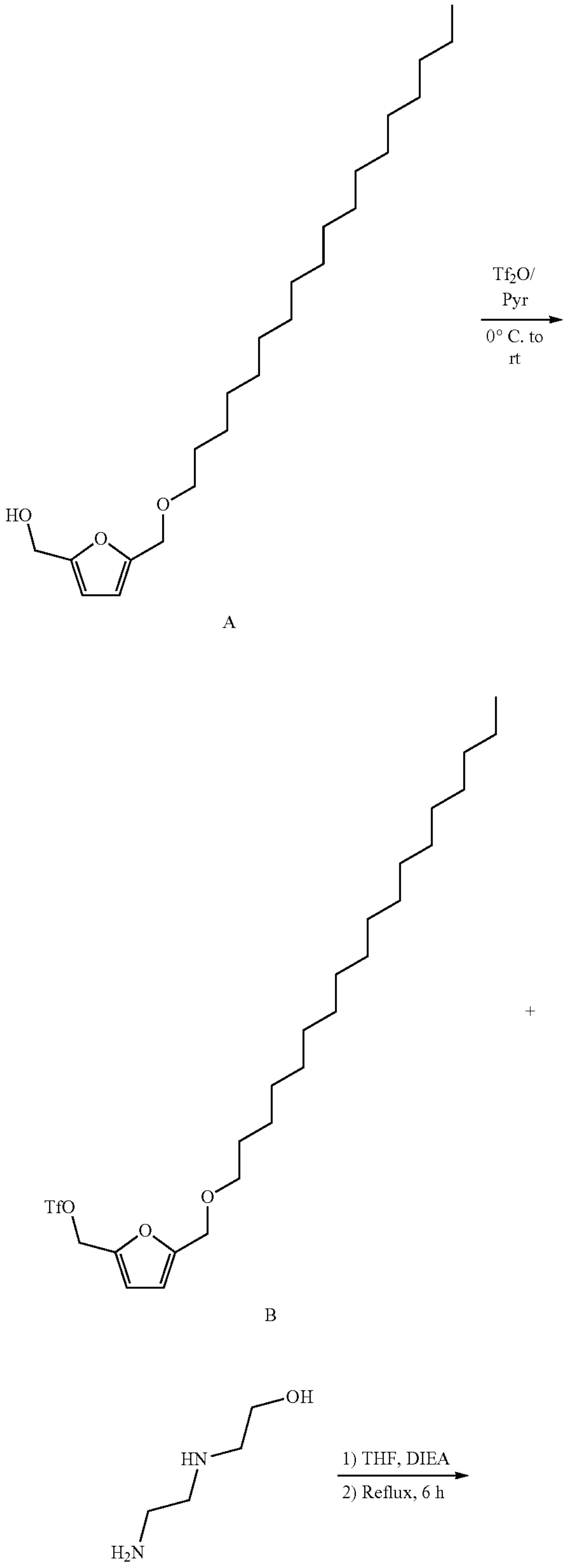

A

B

-continued

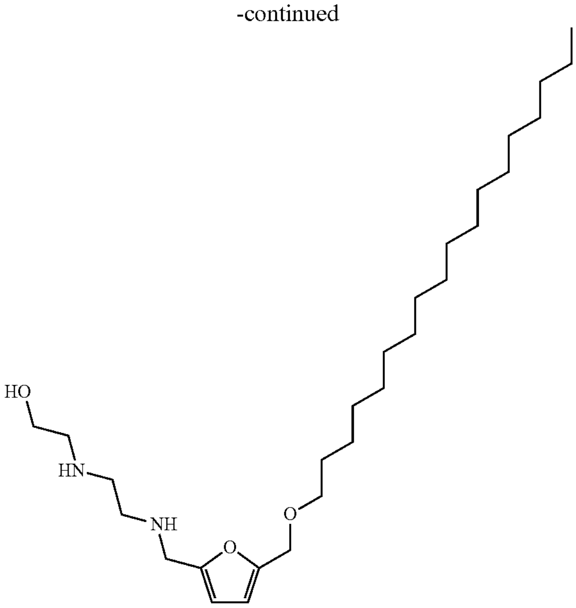

C

Experimental:

An oven dried, single neck 25 mL round bottomed flask equipped with a 0.5" PTFE coated octagonal magnetic stir bar was charged with 100 mg of a (5-((octadecyloxy)methyl)furan-2-yl)methanol A (0.263 mmol), 42 μL of pyridine (0.526 mmol) and 5 mL of anhydrous methylene chloride. The flask was then immersed in an ice-brine bath (~−10° C.) and, while stirring, 44.2 μL of triflic anhydride (0.263 mmol) was added dropwise over 15 minutes. The mixture was then warmed to room temperature and continued to react for 2 hour. After this time, an aliquot was removed and spotted on a silica gel TLC plate that was developed using a 25% ethyl acetate eluent. One spot appeared on the plate (cerium molybdate visualization) with an Rf=0.54. The absence of the band corresponding to the starting alcohol, Rf=0.41, signified complete conversion. Excess solvent was then evaporated, furnishing 110 mg of a light yellow oil (82%) specifying (5-((octadecyloxy)methyl)furan-2-yl)methyl trifluoromethanesulfonate, B. This material was used in the subsequent step without further purification. A single neck 50 mL round bottomed flask equipped with a PTFE coated magnetic stir bar and was charged with 100 mg of (5-((octadecyloxy)methyl)furan-2-yl)methyl trifluoromethanesulfonate B (0.195 mmol), 20.3 mg of 2-((2-aminoethyl)amino)ethanol (0.195 mmol), 67.9 μL of diisopropyl-ethylamine (0.390 mmol) and 10 mL of anhydrous THF. A reflux condenser was outfitted to the flask, and while stirring, the solution was heated to reflux for 6 hours. After this time, an aliquot was extracted and analyzed by TLC (cerium molybdate visualization), demonstrating that B had entirely disappeared. The mixture was poured directly onto a short-path, pre-fabricated column comprised of neutral alumina, where flash chromatography with absolute ethanol afforded 31 mg of 2-((2-(((5-((octadecyloxy)methyl)-furan-2-yl)methyl)amino)ethyl)amino)ethanol C as a loose, pale yellow oil (34%). $^{1}H$ NMR (400 MHz, $CDCl_3$) δ (ppm) 6.38 (d, J=8.2 Hz, 1H), 6.16 (d, J=8.2 Hz, 1H), 4.51 (s, 2H), 3.62 (m, 3H), 3.45 (m, 2H), 3.32 (t, J=6.0 Hz, 2H), 2.94 (m, 2H), 2.80 (m, 2H), 2.61 (m, 4H), 1.59 (m, 2H), 1.42 (m, 2H), 1.33-1.29 (m, 28H), 0.91 (t, J=6.8 Hz, 3H); $^{13}C$ NMR (100 MHz, $CDCl_3$) δ (ppm) 149.9, 149.1, 108.2, 107.0, 73.5, 68.2, 62.1, 51.6, 50.9, 47.8, 46.6, 30.3, 30.0, 29.6, 29.5, 29.4, 29.3, 29.2, 29.0, 28.9, 28.8, 28.7, 28.6, 28.4, 28.2, 28.0, 21.8, 13.8

Example 18: Synthesis of 1-(5-((hexyloxy)methyl)furan-2-yl)-N,N,N-trimethylmethanaminium iodide, D

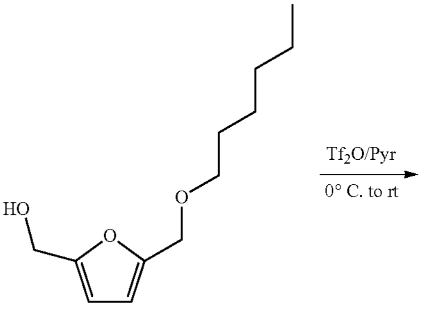

A

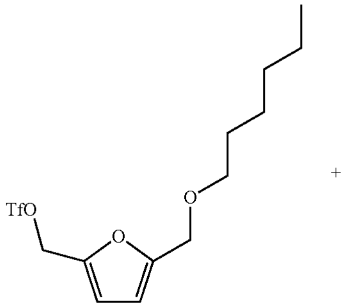

B

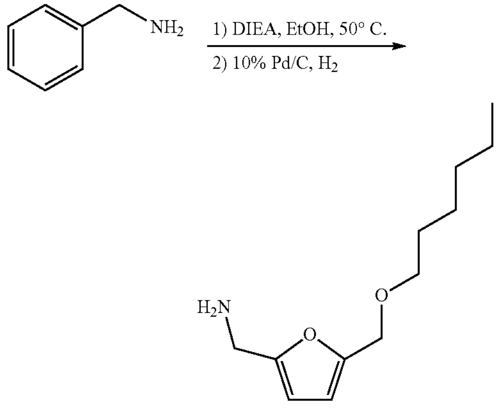

C

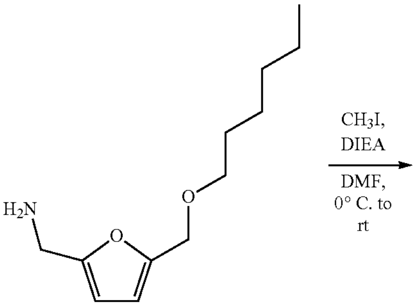

C

-continued

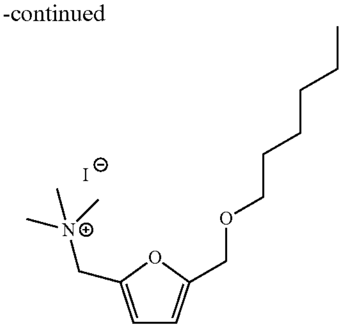

D

Experimental:

An oven dried, 25 mL single neck round bottomed flask equipped with a tapered 1 cm PTFE coated magnetic stir bar was charged with 125 mg of (5-((hexyloxy)methyl)furan-2-yl)methanol A (0.589 mmol), 94 μL of pyridine (1.18 mmol) and 10 mL of anhydrous methylene chloride. The flask was then immersed in brine/ice bath (~−10° C.), and while vigorously stirring, 99.1 μL of triflic anhydride (0.589 mmol) was added dropwise over 10 minutes. The ice bath was then removed and reaction continued at room temperature for 2 hrs. After this time, an aliquot was removed, spotted on a silica gel TLC plate and developed with 20% ethyl acetate in hexanes, indicating (cerium molybdate visualization) a single band with an $R_f$=0.52. The signature band for A, $R_f$=0.39, was patently absent, indicating this reagent had fully converted. Solids were then filtered and filtrate concentrated in vacuo overnight, furnishing 183 mg of (5-((hexyloxy)methyl)furan-2-yl)methyl trifluoromethanesulfonate B as a beige oil (90%). This product was used in the next step without further purification.

A single neck, 25 mL round bottomed flask equipped with a 1 cm PTFE coated magnetic stir bar was charged with 150 mg of (5-((hexyloxy)methyl)furan-2-yl)methyl trifluoromethanesulfonate B (0.436 mmol), 152 μL of Hunig's base (0.871 mmol), 48 μL of benzylamine (0.436 mmol) and 10 mL of ethanol. The neck was capped with a reflux condenser, and while vigorously stirring, the mixture was heated to 50° C. for 2 h. After this time, TLC (UV and cerium molybdate visualization) indicated a single band and full consumption of both reagents. The mixture was then diluted with 10 mL of water and 10 mL of methylene chloride and layers partitioned by liquid-liquid extraction. The aqueous layer was extracted with 5 mL volumes of methylene chloride (×2), organic layers combined and dried, affording a pale yellow waxy solid. This residue was charged to a 25 mL round bottomed flask equipped with a PTFE coated magnetic stir bar, along with 100 mg of 10% Pd/C and 10 mL of absolute ethanol. The neck was capped with a rubber septum and a balloon filled with $H_2$ was inserted via a 9 inch, 16" needle; the mixture was stirred vigorously and monitored by TLC (UV-vis visualization). After 1.5 h, the reaction was deemed complete; catalyst filtered through a pad of Celite and filtrate concentrated under vacuum overnight, affording 71 mg of (5-((hexyloxy)methyl)furan-2-yl) methanamine C (77%) as colorless, loose oil. This product was used in the next step without further purification.

A single neck, 25 mL round bottomed flask equipped with a PTFE coated magnetic stir bar was charged with 50 mg of (5-((hexyloxy)methyl)furan-2-yl)methanamine C (0.237 mmol) and 5 mL of anhydrous DMF. The flask was capped with a rubber septum affixed to an argon inlet and immersed in a saturated brine/ice bath mixture (~0° C.). While vigorously stirring and under argon, 74 μL of methyl iodide (167 mg, 1.18 mmol) the mixture was added dropwise over 10 minutes. Upon complete addition, the ice bath was withdrawn and the mixture stirred at room temperature overnight. After this time, 15 mL of diethyl ether was added, which induced the precipitation of a white solid. The solid was filtered, washed with 5 mL of diethyl ether (×3) and dried high vacuum (<1 torr) for 1 week. After this time, a 55 mg of 1-(5-((hexyloxy)methyl)furan-2-yl)-N,N,N-trimethylmethanaminium iodide D was obtained as a fine white powder (61% of theoretical). $^1H$ NMR (400 MHz, $d^6$-DMSO) δ (ppm) 6.29 (d, J=8.2 Hz, 1H), 6.10 (d, J=8.2 Hz, 1H), 4.42 (s, 2H), 4.30 (s, 2H), 3.51 (s, 9H), 3.40 (t, J=6.2 Hz, 2H), 1.48-1.46 (m, 4H), 1.33-1.31 (m, 4H), 0.91 (s, 3H); $^{13}C$ NMR (100 MHz, $d^6$-DMSO) δ (ppm) 152.7, 151.4, 109.0, 108.2, 73.6, 70.0, 68.8, 50.6, 30.8, 30.1, 23.4, 22.5, 15.8.

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

I claim:

1. A process for preparing linear mono- and di-alkyl ethers of either furan-2,5-dimethanol (FDM) or 2,5-bis(hydroxymethyl)tetrahydrofuran (bHMTHF) comprising: contacting either FDM or bHMTHF in a polar aprotic organic solvent with a permittivity (∈)>8, at a temperature ranging from about −25° C. to about 100° C., with either a) an unhindered Brønsted base having a difference in pKa (ΔpKa)≥15 relative to the pKa of a hydroxyl group of either said FDM or bHMTHF, or b) a hindered Brønsted base and a nucleophile.

2. The process according to claim 1, wherein said unhindered Brønsted base is a metallic hydride.

3. The process according to claim 2, wherein said unhindered Brønsted base is at least one of a lithium, sodium, or potassium hydride.

4. The process according to claim 1, wherein said unhindered Brønsted base is an organometallic base.

5. The process according to claim 4, wherein said unhindered Brønsted base is at least one of an alkyl lithium, alkyl magnesium, or alkyl cuprate compound.

6. The process according to claim 1, wherein said unhindered Brønsted base is a metal amide or Grignard reagent.

7. The process according to claim 1, wherein said hindered Brønsted base is at least one of sodium or potassium t-butoxide, or lithium diisopropylamide.

8. The process according to claim 1, wherein said hindered Brønsted base has a pKa of at least 16.

9. The process according to claim 8, wherein said hindered Brønsted base has a pKa ≥20.

10. The process according to claim 1, wherein said polar, aprotic organic solvent has a permittivity (∈)>30.

11. The process according to claim 1, wherein said polar, aprotic organic solvent is at least one of: dimethylformamide (DMF), dimethylsulfoxide (DMSO), dimethylacetamide (DMA), N-methylpyrrolidone (NMP), hexamethylphosphoramide (HMPA), acetone, acetonitrile (ACN), nitromethane, sulfolane, tetrahydrofuran (THF), 1,4-dioxane, and ethyl acetate.

12. The process according to claim 1, wherein said nucleophile is at least one of:

an alkyl halide or sulfonate with an alkyl chain length between $C_5$-$C_{25}$.

13. The process according to claim 12, wherein said alkyl halide or sulfonate has an alkyl chain length between $C_8$-$C_{18}$.

14. The process according to claim 12, wherein said halide is at least one of: Cl, Br, or I.

15. The process according to claim 12, wherein said sulfonate is at least one of: a -OTf (triflate), -OMs (mesylate), -OTs (tosylate), -OBs (brosylate), or -OEs (esylate).

16. The process according to claim 1, wherein said temperature is in a range from about −10° C. to about 70° C.

17. The process according to claim 1, wherein said temperature is in a range from about −5° C. to about 35° C.

18. The process according to claim 1, wherein said mono- and diethers of FDM and bHMTHF have linear hydrocarbon chain lengths of $C_5$-$C_{25}$.

19. The process according to claim 18, wherein said mono- and diethers of bHMTHF and FDM have linear hydrocarbon chain lengths of $C_6$-$C_{18}$.

20. A method of preparing a mono-ether comprising: contacting FDM with a Brønsted base and 1 or less molar equivalents of an alkyl-X species according to the following:

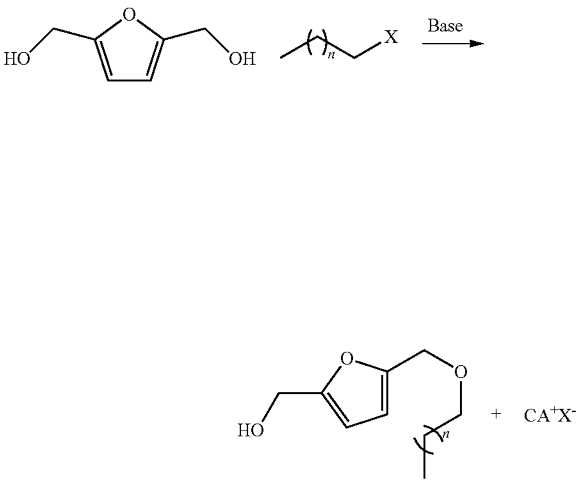

wherein: "X" is the leaving group, "n" is an integer from 5 to 25, and "CA" is a conjugate acid.

21. A mono-ether of FDM prepared according to claim 20, wherein said mono-ether of FDM is at least one of the following compounds:

a. (5-((octadecyloxy)methyl)furan-2-yl)methanol

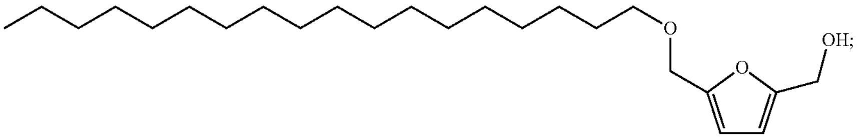 [SMILES: CCCCCCCCCCCCCCCCCCOCc1ccc(CO)o1]

b. (5-((dodecyloxy)methyl)furan-2-yl)methanol

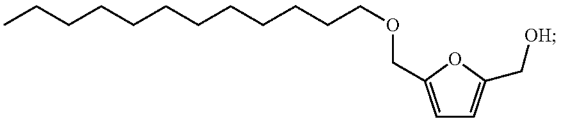 [SMILES: CCCCCCCCCCCCOCc1ccc(CO)o1]

and a. (5-((hexyloxy)methyl)furan-2-yl)methanol

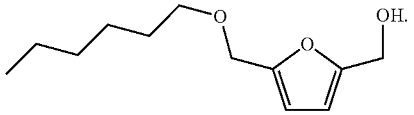

22. A method of preparing a di-ether comprising: contacting FDM with a Brønsted base and a minimum of 2 molar equivalents of an alkyl-X species according to the following:

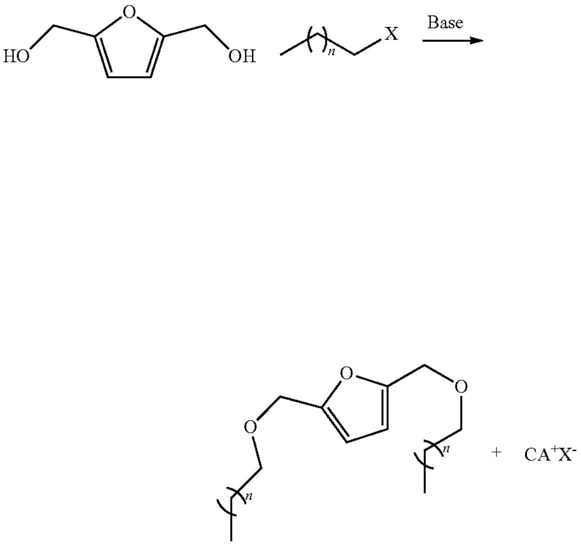

wherein: "X" is the leaving group, "n" is an integer from 5 to 25, and "CA" is a conjugate acid of the base.

23. A di-ether of FDM prepared according to claim 22, wherein said di-ether of FDM is at least one of the following compounds:

a. 2,5-bis((hexyloxy)methyl)furan

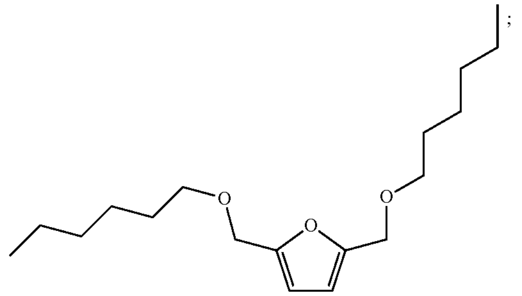 [SMILES: CCCCCCOCc1ccc(COCCCCCC)o1]

b. 2,5-bis((dodecyloxy)methyl)furan

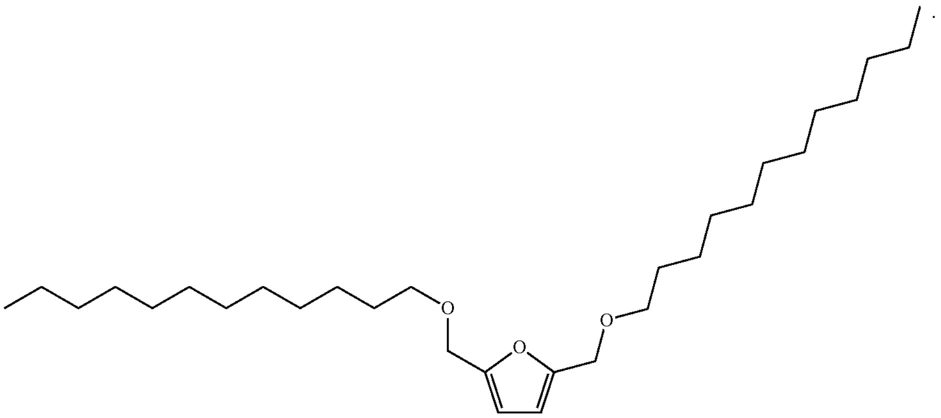 [SMILES: CCCCCCCCCCCCOCc1ccc(COCCCCCCCCCCCC)o1]

24. A method of preparing a mono-ether comprising: contacting bHMTHFs with a Brønsted base and 1 or less molar equivalents of an alkyl-X species according to at least one of the following:

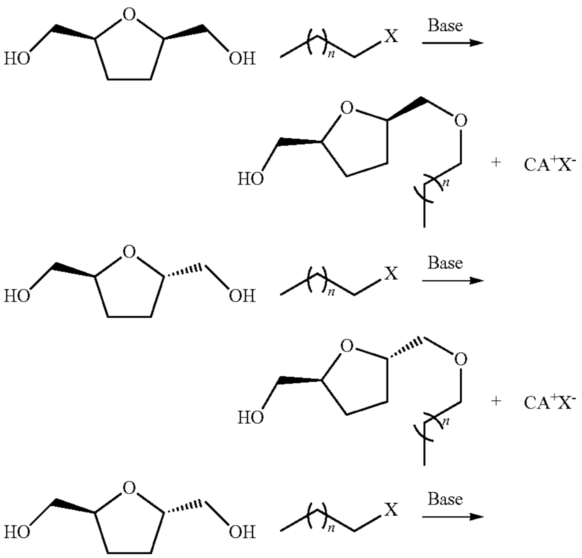

-continued

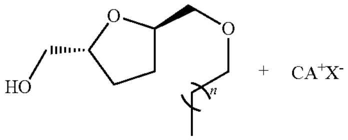

wherein: "X" is the leaving group, "n" is an integer from 5 to 25, and "CA" is a conjugate acid.

25. A mono-ether of bHMTHF prepared according to claim 24, wherein said mono-ether of bHMTHF is at least one of the following compounds:

a. ((2S,5R)-5-((hexyloxy)methyl)tetrahydrofuran-2-yl) methanol

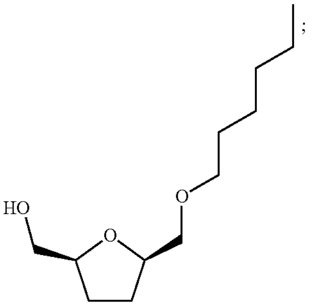

b. ((2S,5S)-5-((hexyloxy)methyl)tetrahydrofuran-2-yl) methanol

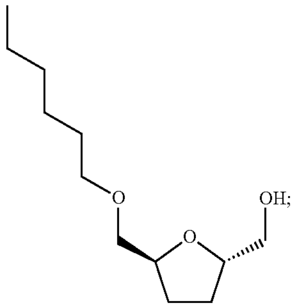

c. ((2S,5S)-5-((hexyloxy)methyl)tetrahydrofuran-2-yl) methanol

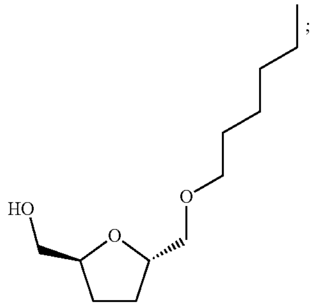

d. ((2S,5R)-5-((dodecyloxy)methyl)tetrahydrofuran-2-yl) methanol

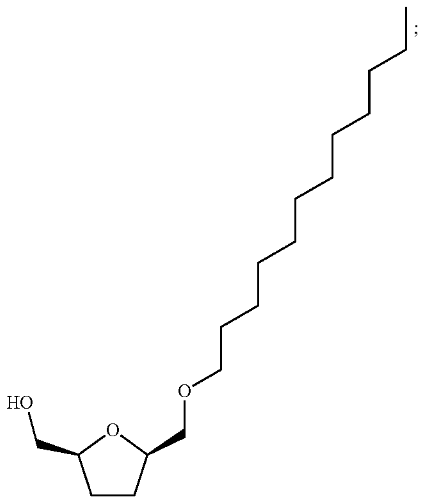 [SMILES: CCCCCCCCCCCCOC[C@H]1CC[C@@H](CO)O1]

e. ((2S,5S)-5-((dodecyloxy)methyl)tetrahydrofuran-2-yl) methanol

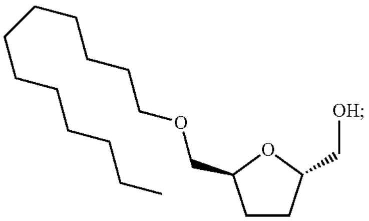 [SMILES: CCCCCCCCCCCCOC[C@@H]1CC[C@@H](CO)O1]

f. ((2S,5S)-5-((dodecyloxy)methyl)tetrahydrofuran-2-yl) methanol

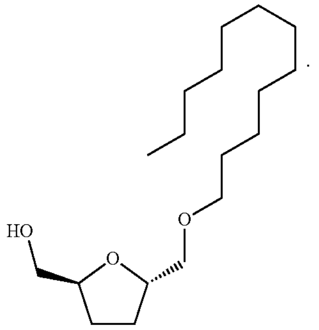 [SMILES: CCCCCCCCCCCCOC[C@@H]1CC[C@@H](CO)O1]

26. A method of preparing a di-ether comprising: contacting bHMTHFs with a Brønsted base and a minimum of 2 molar equivalents of an alkyl-X species according to the following:

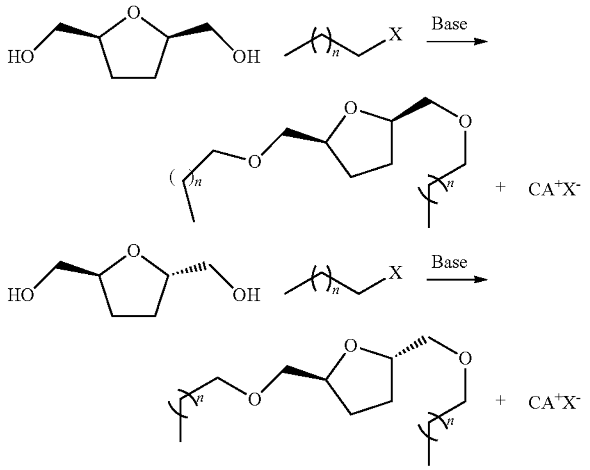

wherein: "X" is the leaving group, "n" is an integer from 5 to 25, and "CA" is a conjugate acid.

27. A di-ether of bHMTHF prepared according to claim 26, wherein said di-ether of bHMTHF is at least one of the following compounds:

a. (2R,5S)-2,5-bis((hexyloxy)methyl)tetrahydrofuran

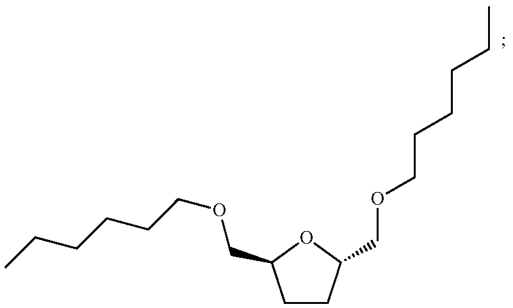 [SMILES: CCCCCCOC[C@@H]1CC[C@@H](COCCCCCC)O1]

b. (2S,5S)-2,5-bis((hexyloxy)methyl)tetrahydrofuran
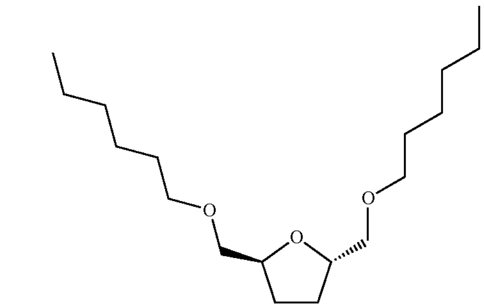
;
c. (2R,5S)-2,5-bis((dodecyloxy)methyl)tetrahydrofuran
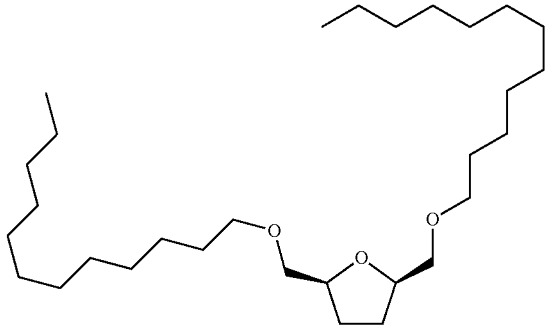
;
d. (2S,5S)-2,5-bis((dodecyloxy)methyl)tetrahydrofuran
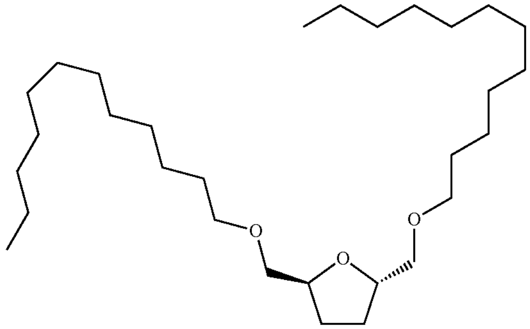
;
e. (2R,5S)-2,5-bis((octadecyloxy)methyl)tetrahydrofuran
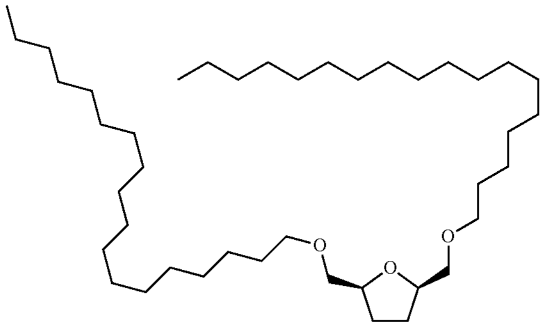
;
and
f. (2S,5S)-2,5-bis((octadecyloxy)methyl)tetrahydrofuran
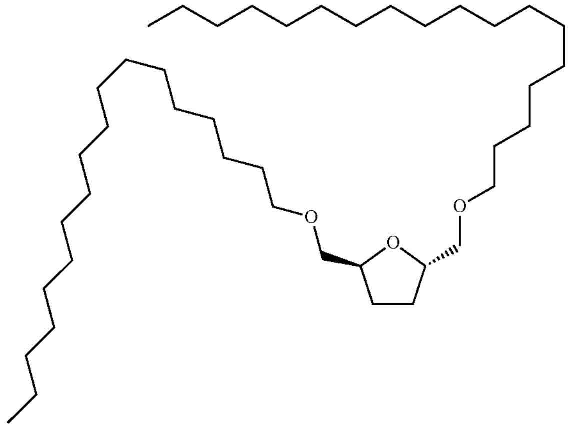
.
* * * * *